(12) United States Patent
Mundlos et al.

(10) Patent No.: US 9,012,401 B2
(45) Date of Patent: Apr. 21, 2015

(54) GROWTH FACTOR MUTANTS WITH IMPROVED BIOLOGICAL ACTIVITY

(75) Inventors: Stefan Mundlos, Berlin (DE); Petra Knaus, Berlin (DE); Jens Pohl, Hambrücken (DE); Michael Kruse, Mainz (DE); Frank Plöger, Wiesbaden (DE)

(73) Assignees: Biopharm Gesellschaft zur biotechnolgischen Entwicklung von Pharmaka mbH, Heidelberg (DE); Charite-Universitatsmedizin Berlin, Berlin (DE); Freie Universitat Berlin, Berlin (DE)

( * ) Notice: Subject to any disclaimer, the term of this patent is extended or adjusted under 35 U.S.C. 154(b) by 1657 days.

(21) Appl. No.: 11/817,735

(22) PCT Filed: Mar. 3, 2006

(86) PCT No.: PCT/EP2006/001966
§ 371 (c)(1),
(2), (4) Date: Feb. 14, 2008

(87) PCT Pub. No.: WO2006/094722
PCT Pub. Date: Sep. 14, 2006

(65) Prior Publication Data
US 2008/0260830 A1    Oct. 23, 2008

(30) Foreign Application Priority Data

Mar. 4, 2005   (EP) .................................... 05004840

(51) Int. Cl.
| | | |
|---|---|---|
| *A61K 38/18* | (2006.01) | |
| *A61K 38/16* | (2006.01) | |
| *C12N 5/00* | (2006.01) | |
| *C07K 14/475* | (2006.01) | |
| *A61K 38/00* | (2006.01) | |

(52) U.S. Cl.
CPC ............... *C07K 14/475* (2013.01); *A61K 38/00* (2013.01)

(58) Field of Classification Search
None
See application file for complete search history.

(56) References Cited

U.S. PATENT DOCUMENTS

| | | |
|---|---|---|
| 5,994,094 A | 11/1999 | Hotten et al. |
| 2002/0169292 A1 | 11/2002 | Weintraub et al. |

FOREIGN PATENT DOCUMENTS

| | | | |
|---|---|---|---|
| WO | WO 95/04819 A1 | 2/1995 | |
| WO | 00/20607 A2 | 4/2000 | |
| WO | WO 2009086131 * | 7/2009 | ............. C07K 14/51 |

OTHER PUBLICATIONS

Guo et al. 2004. PNAS. 101:9205-9210.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
http://www.peprotech.com/content/focusarticles.htm?id=69, 2005, downloaded Jun. 28, 2011.*
Phillips et al. 2006. The Spine J. 6:500-506.*
Seemann et al., "Activating and deactivating mutations in the receptor interaction site of GDF5 cause symphalangism or brachydactyly type A2", The Journal of Clinical Investigation, vol. 115, No. 9, Sep. 2005, pp. 2373-2381.
Dawson et al., "GDF5 is a Second Locus for Multiple-Synostosis Syndrome", The American Journal of Human Genetics, vol. 78, Apr. 2006, pp. 708-712.
Panopoulou et al., "AmphiBMP 2/4, an Amphioxus Bone Morphogenetic Protein Closely Related to *Drosophila* decapentaplegic and Vertebrate BMP2 and BMP4: Insights into Evolution of Dorsoventral Axis Specification", Developmental Dynamics 213: 130-139 (1998).
Stenzel et al., "The Univin Gene Encodes a Member of the Transforming Growth Factor-β Superfamily with Restricted Expression in the Sea Urchin Embryo", Developmental Biology, 166, 149-158 (1994).
Oppermann et al., "Human OP-1 mutant protein H2177", XP-002358154, 2 pgs, 2007.

* cited by examiner

*Primary Examiner* — Shulamith H Shafer
(74) *Attorney, Agent, or Firm* — Rothwell, Figg, Ernst & Manbeck, P.C.

(57) ABSTRACT

The invention relates to novel biosynthetic growth factor mutants which exhibit improved biological activity.

14 Claims, 9 Drawing Sheets

1 MRLPKLLTFL LWYLAWLDLE FICTVLGAPD LGQRPQGTRP GLAKAEAKER PPLARNVFRP
61 GGHSYGGGAT NANARAKGGT GQTGGLTQPK KDEPKKLPPR PGGPEPKPGH PPQTRQATAR
121 TVTPKGQLPG GKAPPKAGSV PSSFLLKKAR EPGPPREPKE PFRPPPITPH EYMLSLYRTL
181 SDADRKGGNS SVKLEAGLAN TITSFIDKGQ DDRGPVVRKQ RYVFDISALE KDGLLGAELR
241 ILRKKPSDTA KPAAPGGGRA AQLKLSSCPS GRQPASLLDV RSVPGLDGSG WEVFDIWKLF
301 RNFKNSAQLC LELEAWERGR AVDLRGLGFD RAARQVHEKA LFLVFGRTKK RDLFFNEIKA
361 RSGQDDKTVY EYLFSQRRKR RAPLATRQGK RPSKNLKARC SRKALHVNFK DMGWDDWIIA
421 PLEYEAFHCE GLCEFPLRSH LEPTNHAVIQ TLMNSMDPES TPPTCCVPTR LSPISILFID
481 SANNVVYKQY EDMVVESCGC R

% sequence identity to
cystine-knot-domain of human GDF-5

| Sequence | % Identity | Identical Residues |
|---|---|---|
| GDF-5 Homo | 100 | 102/102 |
| GDF-5 Mus | 99 | 101/102 |
| GDF-5 Gallus | 99 | 101/102 |
| GDF-5 Xenopus | 94 | 96/102 |
| GDF-5 Danio (Contact) | 88 | 90/102 |
| GDF-7 Danio | 88 | 90/102 |
| GDF-6 Mus | 86 | 88/102 |
| GDF-7 Gallus | 86 | 88/102 |
| GDF-6 Danio (Radar) | 86 | 88/102 |
| GDF-6 Homo | 85 | 87/102 |
| GDF-6 Xenopus | 84 | 86/102 |
| GDF-6 Bos | 83 | 85/102 |
| GDF-7 Homo | 81 | 83/102 |
| GDF-7 Cercopithecus | 80 | 82/102 |
| GDF-7 Macaca | 80 | 82/102 |
| GDF-7 Mus | 80 | 82/102 |
| GDF-6 Danio (Dynamo) | 79 | 81/102 |
| BMP-2A | 57 | 58/102 |
| BMP-2B | 57 | 58/102 |
| Vg-1 | 52 | 53/102 |
| DPP | 52 | 53/102 |
| BMP-5 | 52 | 53/102 |
| BMP-9 | 51 | 52/102 |
| BMP-10 | 51 | 52/102 |
| BMP-8A | 51 | 51/102 |
| BMP-6 | 51 | 52/102 |
| BMP-7 | 51 | 52/102 |
| GDF-3 | 49 | 50/102 |
| 60A | 48 | 49/102 |
| BMP-8B | 48 | 49/102 |
| BMP-3A | 47 | 48/103 |
| GDF-9B | 45 | 46/102 |
| BMP-3B | 43 | 44/103 |
| GDF-8 | 37 | 38/102 |
| GDF-12 | 37 | 38/104 |
| GDF-11 | 36 | 37/102 |
| GDF-9 | 32 | 33/102 |

FIG 4

SEQUENCE LISTING

<160> NUMBER OF SEQ ID NOS: 35

<210> SEQ ID NO 1
<211> LENGTH: 501
<212> TYPE: PRT
<213> ORGANISM: Homo sapiens

<400> SEQUENCE: 1

```
Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270
```

```
Gln Pro Ala Ser Leu Leu Asp Val Arg Ser Val Pro Gly Leu Asp Gly
            275                 280                 285

Ser Gly Trp Glu Val Phe Asp Ile Trp Lys Leu Phe Arg Asn Phe Lys
        290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 2
<211> LENGTH: 2703
<212> TYPE: DNA
<213> ORGANISM: Homo sapiens

<400> SEQUENCE: 2
ccatggcctc gaaagggcag cggtgatttt tttcacataa atatatcgca cttaaatgag    60
tttagacagc atgacatcag agagtaatta aattggtttg ggttggaatt ccgtttccaa   120
ttcctgagtt caggtttgta aaagattttt ctgagcacct gcaggcctgt gagtgtgtgt   180
gtgtgtgtgt gtgtgtgtgt gtgtgtgtga agtattttca ctggaaagga ttcaaaacta   240
gggggaaaaa aaaactggag cacacaggca gcattacgcc attcttcctt cttggaaaaa   300
tccctcagcc ttatacaagc ctccttcaag ccctcagtca gttgtgcagg agaaagggggg   360 cggttggctt tctcctttca agaacgagtt attttcagct gctgactgga gacggtgcac   420
gtctggatac gagagcattt ccactatggg actggataca acacacacc cggcagactt   480 caagagtctc agactgagga gaaagccttt ccttctgctg ctactgctgc tgccgctgct   540
tttgaaagtc cactcctttc atggttttc ctgccaaacc agaggcacct ttgctgctgc   600
cgctgttctc tttggtgtca ttcagcggct ggccagagga tgagactccc caaactcctc   660
actttcttgc tttggtacct ggcttggctg gacctggaat tcatctgcac tgtgttgggt   720
gcccctgact tgggccagag accccagggg accaggccag gattggccaa agcagaggcc   780
```

```
aaggagaggc ccccctggc ccggaacgtc ttcaggccag ggggtcacag ctatggtggg    840
ggggccacca atgccaatgc cagggcaaag ggaggcaccg ggcagacagg aggcctgaca    900
cagcccaaga aggatgaacc caaaaagctg ccccccagac cgggcggccc tgaacccaag    960
ccaggacacc ctcccaaac aaggcaggct acagcccgga ctgtgacccc aaaaggacag   1020
cttcccggag gcaaggcacc cccaaaagca ggatctgtcc ccagctcctt cctgctgaag   1080
aaggccaggg agcccgggcc cccacgagag cccaaggagc cgtttcgccc accccccatc   1140 acacccacg agtacatgct ctcgctgtac aggacgctgt ccgatgctga cagaaaggga   1200
ggcaacagca gcgtgaagtt ggaggctggc ctggccaaca ccatcaccag ctttattgac   1260
aaagggcaag atgaccgagg tcccgtggtc aggaagcaga ggtacgtgtt tgacattagt   1320
gccctggaga aggatgggct gctggggggcc gagctgcgga tcttgcggaa gaagccctcg   1380
gacacggcca agccagcggc ccccggaggc gggcgggctg cccagctgaa gctgtccagc   1440
tgccccagcg gccggcagcc ggcctccttg ctggatgtgc gctccgtgcc aggcctggac   1500
ggatctggct gggaggtgtt cgacatctgg aagctcttcc gaaactttaa gaactcggcc   1560
cagctgtgcc tggagctgga ggcctgggaa cggggcaggg ccgtggacct ccgtggcctg   1620
ggcttcgacc gcgccgcccg gcaggtccac gagaaggccc tgttcctggt gtttggccgc   1680
accaagaaac gggaccctgtt ctttaatgag attaaggccc gctctggcca ggacgataag   1740
accgtgtatg agtacctgtt cagccagcgg cgaaaacggc gggcccact ggccactcgc   1800 cagggcaagc gacccagcaa gaaccttaag gctcgctgca gtcggaaggc actgcatgtc   1860
aacttcaagg acatgggctg ggacgactgg atcatcgcac cccttgagta cgaggctttc   1920
cactgcgagg ggctgtgcga gttcccattg cgctcccacc tggagcccac gaatcatgca   1980
gtcatccaga ccctgatgaa ctccatggac cccgagtcca caccacccac ctgctgtgtg   2040
cccacgcggc tgagtcccat cagcatcctc ttcattgact ctgccaacaa cgtggtgtat   2100
aagcagtatg aggacatggt cgtggagtcg tgtggctgca ggtagcagca ctggccctct   2160
gtcttcctgg gtggcacatc ccaagagccc cttcctgcac tcctggaatc acagaggggt   2220
caggaagctg tggcaggagc atctacacag cttgggtgaa aggggattcc aataagcttg   2280
ctcgctctct gagtgtgact tgggctaaag gcccctttt atccacaagt tcccctggct   2340
gaggattgct gcccgtctgc tgatgtgacc agtggcaggc acaggtccag ggagacagac   2400
tctgaatggg actgagtccc aggaaacagt gctttccgat gagactcagc ccaccatttc   2460
tcctcacctg ggccttctca gcctctggac tctcctaagc acctctcagg agagccacag   2520
gtgccactgc ctcctcaaat cacatttgtg cctggtgact tcctgtccct gggacagttg   2580
agaagctgac tggcaagag tgggagagaa gaggagaggg cttggataga gttgaggagt   2640
gtgaggctgt tagactgtta gatttaaatg tatattgatg agataaaag caaaactgtg   2700 cct                                                                2703
```

<210> SEQ ID NO 3
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: X IS ANY AMINO ACID
<220> FEATURE:
<221> NAME/KEY: MISC_FEATURE
<222> LOCATION: (39)..(39)

<223> OTHER INFORMATION: X DENOTES ALANINE(A), ASPARAGINE(N),
      GLYCINE(G), ISOLEUCINE(I), LEUCINE(L), METHIONINE(M), OR VALINE(V)

<400> SEQUENCE: 3

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Ser His Leu Glu Pro Thr Asn His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 4
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: X DENOTES ANY AMINO ACID
<220> FEATURE:
<221> NAME/KEY: MISC_FEATURE
<222> LOCATION: (40)..(40)
<223> OTHER INFORMATION: X DENOTES ASPARTIC ACID(D), GLUTAMIC ACID(E),
      GLYCINE(G), LEUCINE(L), OR ISOLEUCINE(I)

<400> SEQUENCE: 4

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Xaa His Leu Glu Pro Thr Asn His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 5
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: X DENOTES ANY AMINO ACID
<220> FEATURE:
<221> NAME/KEY: MISC_FEATURE
<222> LOCATION: (46)..(46)
<223> OTHER INFORMATION: X DENOTES SERINE(S) OR THREONINE(T)

<400> SEQUENCE: 5

```
Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25              30

Xaa Cys Xaa Phe Pro Xaa Arg Ser His Leu Glu Pro Thr Xaa His Ala
        35              40                  45

Xaa Ile Gln Thr Leu Xaa Asn Ser Met Xaa Pro Xaa Xaa Xaa Pro Xaa
    50                  55              60

Xaa Cys Cys Val Pro Xaa Xaa Leu Xaa Pro Ile Ser Ile Leu Xaa Xaa
65              70              75                      80

Asp Xaa Xaa Asn Asn Val Val Tyr Xaa Xaa Tyr Glu Xaa Met Val Val
            85                  90              95

Glu Xaa Cys Gly Cys Arg
            100
```

<210> SEQ ID NO 6
<211> LENGTH: 102
<212> TYPE: PRT
<213> ORGANISM: Homo Sapiens
<220> FEATURE:
<221> NAME/KEY: MISC_FEATURE
<222> LOCATION: (1)..(102)
<223> OTHER INFORMATION: X DENOTES ANY AMINO ACID
<220> FEATURE:
<221> NAME/KEY: MISC_FEATURE
<222> LOCATION: (39)..(39)
<223> OTHER INFORMATION: X DENOTES ALANINE(A), ASPARAGINE(N),
      GLYCINE(G), ISOLEUCINE(I), LEUCINE(L), METHIONINE(M), OR VALINE(V)
<220> FEATURE:
<221> NAME/KEY: MISC_FEATURE
<222> LOCATION: (40)..(40)
<223> OTHER INFORMATION: X DENOTES ASPARTIC ACID(D), GLUTAMIC ACID(E),
      GLYCINE(G), LEUCINE(L), OR ISOLEUCINE(I)

<400> SEQUENCE: 6

```
Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25              30

Xaa Cys Xaa Phe Pro Xaa Xaa Xaa His Leu Glu Pro Thr Asn His Ala
        35              40                  45

Xaa Ile Gln Thr Leu Xaa Asn Ser Met Xaa Pro Xaa Xaa Xaa Pro Xaa
    50                  55              60

Xaa Cys Cys Val Pro Xaa Xaa Leu Xaa Pro Ile Ser Ile Leu Xaa Xaa
65              70              75                      80

Asp Xaa Xaa Asn Asn Val Val Tyr Xaa Xaa Tyr Glu Xaa Met Val Val
            85                  90              95

Glu Xaa Cys Gly Cys Arg
            100
```

<210> SEQ ID NO 7
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: X DENOTES ANY AMINO ACID
<220> FEATURE:
<221> NAME/KEY: MISC_FEATURE
<222> LOCATION: (39)..(39)
<223> OTHER INFORMATION: X DENOTES ALANINE(A), ASPARAGINE(N),
      GLYCINE(G), ISOLEUCINE(I), LEUCINE(L), METHIONINE(M), OR

```
              VALINE(V)
<220> FEATURE:
<221> NAME/KEY: MISC_FEATURE
<222> LOCATION: (46)..(46)
<223> OTHER INFORMATION: X DENOTES SERINE(S) OR THREONINE(T)

<400> SEQUENCE: 7

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Ser His Leu Glu Pro Thr Xaa His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 8
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: X DENOTES ANY AMINO ACID
<220> FEATURE:
<221> NAME/KEY: MISC_FEATURE
<222> LOCATION: (40)..(40)
<223> OTHER INFORMATION: X DENOTES ASPARTIC ACID(D), GLUTAMIC ACID(E),
      GLYCINE(G), LEUCINE(L), OR ISOLEUCINE(I)
<220> FEATURE:
<221> NAME/KEY: MISC_FEATURE
<222> LOCATION: (46)..(46)
<223> OTHER INFORMATION: X DENOTES SERINE(S) OR THREONINE(T)

<400> SEQUENCE: 8

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Xaa His Leu Glu Pro Thr Xaa His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 9
<211> LENGTH: 102
<212> TYPE: PRT
<213> ORGANISM: Homo Sapiens
<220> FEATURE:
<221> NAME/KEY: MISC_FEATURE
<222> LOCATION: (1)..(102)
```

-continued

<223> OTHER INFORMATION: X IS ANY AMINO ACID
<220> FEATURE:
<221> NAME/KEY: MISC_FEATURE
<222> LOCATION: (39)..(39)
<223> OTHER INFORMATION: X DENOTES ALANINE(A), ASPARAGINE(N),
      GLYCINE(G), ISOLEUCINE(I), LEUCINE(L), METHIONINE(M), OR
      VALINE(V)
<220> FEATURE:
<221> NAME/KEY: MISC_FEATURE
<222> LOCATION: (40)..(40)
<223> OTHER INFORMATION: X DENOTES ASPARTIC ACID(D), GLUTAMIC ACID(E),
      GLYCINE(G), LEUCINE(L), OR ISOLEUCINE(I)
<220> FEATURE:
<221> NAME/KEY: MISC_FEATURE
<222> LOCATION: (46)..(46)
<223> OTHER INFORMATION: X DENOTES SERINE(S) OR THREONINE(T)

<400> SEQUENCE: 9

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Xaa His Leu Glu Pro Thr Xaa His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 10
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P),
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:

```
-continued

<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (39)..(39)
<223> OTHER INFORMATION: X DENOTES ALANINE(A) ASPARAGINE (N) GLYCINE
      (G), ISOLEUCINE (I) LEUCINE (L) METHIONINE (M) OR VALINE (V)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES ALANINE(A), ISOLEUCINE(I), OR
      VALINE(V)
<220> FEATURE:
<221> NAME/KEY: MISC_FEATURE
<222> LOCATION: (54)..(54)
<223> OTHER INFORMATION: X DENOTES LEUCINE (L) OR METHIONINE (M)
<220> FEATURE:
<221> NAME/KEY: MISC_FEATURE
<222> LOCATION: (58)..(58)
<223> OTHER INFORMATION: X DENOTES ALANINE(A), ASPARAGINE(N), OR
      ASPARTIC ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N),
      ASPARTIC ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S), OR
      THREONINE(T)
<220> FEATURE:
<221> NAME/KEY: MISC_FEATURE
<222> LOCATION: (71)..(71)
```

```
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S)
      OR THREONINE(T)

<400> SEQUENCE: 10

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Ser His Leu Glu Pro Thr Asn His Ala
        35                  40                  45

Xaa Ile Gln Thr Leu Xaa Asn Ser Met Xaa Pro Xaa Xaa Xaa Pro Xaa
50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 11
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P)
```

```
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F), OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (40)..(40)
<223> OTHER INFORMATION: X DENOTES ASPARTIC ACID (D), GLUTAMIC ACID (E),
      GLYCINE (G), LEUCINE (L), OR ISOLEUCINE (I)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES LEUCINE (L) OR METHIONINE (M)
<220> FEATURE:
<221> NAME/KEY: MISC_FEATURE
<222> LOCATION: (58)..(58)
<223> OTHER INFORMATION: X DENOTES ALANINE(A), ASPARAGINE(N) OR ASPARTIC
      ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
```

```
                         THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S) OR THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S),
      OR THREONINE(T)

<400> SEQUENCE: 11

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Xaa His Leu Glu Pro Thr Asn His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100
```

-continued

```
<210> SEQ ID NO 12
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P)
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M) OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (46)..(46)
<223> OTHER INFORMATION: X DENOTES SERINE (S) OR THREONINE (T)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES LEUCINE (L) OR METHIONINE (M)
<220> FEATURE:
<221> NAME/KEY: MISC_FEATURE
<222> LOCATION: (58)..(58)
<223> OTHER INFORMATION: X DENOTES ALANINE(A), ASPARAGINE(N) OR ASPARTIC
```

```
            ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S)
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M) OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S) OR THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S),
      OR THREONINE(T)

<400> SEQUENCE: 12

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Ser His Leu Glu Pro Thr Xaa His Ala
```

```
              35                  40                  45
Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 13
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P),
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
```

-continued

```
<221> NAME/KEY: MISC_FEATURE
<222> LOCATION: (39)..(39)
<223> OTHER INFORMATION: X DENOTES ALANINE (A), ASPARAGINE(N),
      GLYCINE(G), ISOLEUCINE(I), LEUCINE(L), METHIONINE(M), OR VALINE(V)
<220> FEATURE:
<221> NAME/KEY: MISC_FEATURE
<222> LOCATION: (40)..(40)
<223> OTHER INFORMATION: X DENOTES ASPARTIC ACID(D), GLUTAMIC ACID(E),
      GLYCINE(G), LEUCINE(L), OR ISOLEUCINE(I)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES LEUCINE(L) OR METHIONINE(M)
<220> FEATURE:
<221> NAME/KEY: MISC_FEATURE
<222> LOCATION: (58)..(58)
<223> OTHER INFORMATION: X DENOTES ALANINE(A), ASPARAGINE(N), OR
      ASPARTIC ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S), OR
      THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
```

```
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S)
      OR THREONINE(T)

<400> SEQUENCE: 13

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Xaa His Leu Glu Pro Thr Asn His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 14
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P),
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
```

```
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (39)..(39)
<223> OTHER INFORMATION: X DENOTES ALANINE(A), ASPARAGINE(N),
      GLYCINE(G), ISOLEUCINE(I), LEUCINE(L), METHIONINE(M), OR VALINE(V)
<220> FEATURE:
<221> NAME/KEY: MISC_FEATURE
<222> LOCATION: (46)..(46)
<223> OTHER INFORMATION: X DENOTES ASPARTIC ACID(D), GLUTAMIC ACID(E),
      GLYCINE(G), LEUCINE(L). OR ISOLEUCINE(I)
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: MISC_FEATURE
<222> LOCATION: (54)..(54)
<223> OTHER INFORMATION: X DENOTES LEUCINE(L) OR METHIONINE(M)
<220> FEATURE:
<221> NAME/KEY: MISC_FEATURE
<222> LOCATION: (58)..(58)
<223> OTHER INFORMATION: X DENOTES ALANINE(A), ASPARAGINE(N), OR
      ASPARTIC ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S), OR
      THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
```

```
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: misc_feature
<222> LOCATION: (98)..(98)
<223> OTHER INFORMATION: Xaa can be any naturally occurring amino acid

<400> SEQUENCE: 14

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Ser His Leu Glu Pro Thr Xaa His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100

<210> SEQ ID NO 15
<211> LENGTH: 102
<212> TYPE: PRT
<213> ORGANISM: Homo Sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P),
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
```

```
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (40)..(40)
<223> OTHER INFORMATION: X DENOTES ASPARTIC ACID(D), GLUTAMIC ACID (E),
      GLYCINE (G), LEUCINE (L) OR ISOLEUCINE (I)
<220> FEATURE:
<221> NAME/KEY: MISC_FEATURE
<222> LOCATION: (46)..(46)
<223> OTHER INFORMATION: X DENOTES SERINE (S) OR THREONINE (T)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES LEUCINE(L) OR METHIONINE(M)
<220> FEATURE:
<221> NAME/KEY: MISC_FEATURE
<222> LOCATION: (58)..(58)
<223> OTHER INFORMATION: X DENOTES ALANINE(A), ASPARAGINE(N), OR
      ASPARTIC ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N),
      ASPARTIC ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
```

```
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S), OR
      THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S)
      OR THREONINE(T)

<400> SEQUENCE: 15

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Xaa His Leu Glu Pro Thr Xaa His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100
```

```
<210> SEQ ID NO 16
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P),
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (39)..(39)
<223> OTHER INFORMATION: X DENOTES ALANINE(A), ASPARAGINE(N),
      GLYCINE(G), ISOLEUCINE(I), LEUCINE(L), METHIONINE(M), OR VALINE(V)
<220> FEATURE:
<221> NAME/KEY: MISC_FEATURE
<222> LOCATION: (40)..(40)
<223> OTHER INFORMATION: X DENOTES ALANINE(A), ASPARAGINE(N),
      GLYCINE(G), ISOLEUCINE(I), LEUCINE(L), METHIONINE(M), OR VALINE(V)
<220> FEATURE:
<221> NAME/KEY: MISC_FEATURE
<222> LOCATION: (46)..(46)
<223> OTHER INFORMATION: X DENOTES SERINE(S) OR THREONINE(T)
<220> FEATURE:
<221> NAME/KEY: MISC_FEATURE
```

-continued

```
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES LEUCINE(L) OR METHIONINE(M)
<220> FEATURE:
<221> NAME/KEY: MISC_FEATURE
<222> LOCATION: (58)..(58)
<223> OTHER INFORMATION: X DENOTES ALANINE(A), ASPARAGINE(N), OR
      ASPARTIC ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N),
      ASPARTIC ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S), OR
      THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S)
```

```
       OR THREONINE(T)

<400> SEQUENCE: 16

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Xaa Xaa His Leu Glu Pro Thr Xaa His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
            85                  90                  95

Glu Xaa Cys Gly Cys Arg
            100

<210> SEQ ID NO 17
<211> LENGTH: 102
<212> TYPE: PRT
<213> ORGANISM: Homo sapiens

<400> SEQUENCE: 17

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Ile Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
            85                  90                  95

Glu Ser Cys Gly Cys Arg
            100

<210> SEQ ID NO 18
<211> LENGTH: 102
<212> TYPE: PRT
<213> ORGANISM: Homo sapiens

<400> SEQUENCE: 18

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Ile Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
            85                  90                  95
```

Glu Ala Cys Gly Cys Arg
            100

<210> SEQ ID NO 19
<211> LENGTH: 102
<212> TYPE: PRT
<213> ORGANISM: Homo sapiens

<400> SEQUENCE: 19

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 20
<211> LENGTH: 102
<212> TYPE: PRT
<213> ORGANISM: Mus musculus

<400> SEQUENCE: 20

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 21
<211> LENGTH: 102
<212> TYPE: PRT
<213> ORGANISM: Gallus gallus

<400> SEQUENCE: 21

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Tyr His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
 50                  55                  60

Thr Cys Cys Val Pro Thr Arg Leu Ser Pro Ile Ser Ile Leu Phe Ile
 65                  70                  75                  80

Asp Ser Ala Asn Asn Val Val Tyr Lys Gln Tyr Glu Asp Met Val Val
                 85                  90                  95

Glu Ser Cys Gly Cys Arg
            100

<210> SEQ ID NO 22
<211> LENGTH: 102
<212> TYPE: PRT
<213> ORGANISM: Danio rerio

<400> SEQUENCE: 22

Cys Asn Arg Lys Gln Leu His Val Asn Phe Lys Glu Met Gly Trp Asp
 1               5                  10                  15

Asp Trp Ile Ile Ala Pro Leu Glu Tyr Glu Ala Phe His Cys Asp Gly
                 20                  25                  30

Val Cys Asp Phe Pro Ile Arg Ser His Leu Glu Pro Thr Asn His Ala
             35                  40                  45

Ile Ile Gln Thr Leu Met Asn Ser Met Asp Pro Glu Ser Thr Pro Pro
 50                  55                  60

Thr Cys Cys Val Pro Thr Arg Leu Ser Pro Ile Ser Ile Leu Tyr Ile
 65                  70                  75                  80

Asp Ser Ala Asn Asn Val Val Tyr Lys Gln Tyr Glu Asp Met Val Val
                 85                  90                  95

Glu Ser Cys Gly Cys Arg
            100

<210> SEQ ID NO 23
<211> LENGTH: 100
<212> TYPE: PRT
<213> ORGANISM: Xenopus laevis

<400> SEQUENCE: 23

Cys Ser Lys Lys Pro Leu His Val Asn Phe Lys Asp Met Gly Trp Asp
 1               5                  10                  15

Asp Trp Ile Ile Ala Pro Leu Glu Tyr Glu Ala Tyr His Cys Glu Gly
                 20                  25                  30

Leu Cys Glu Phe Pro Leu Arg Ser His Leu Glu Pro Thr Asn His Ala
             35                  40                  45

Val Ile Gln Thr Leu Met Asn Ser Met Asp Pro Gly Thr Thr Pro Pro
 50                  55                  60

Thr Cys Cys Val Pro Thr Arg Leu Ser Pro Ile Ser Ile Leu Tyr Thr
 65                  70                  75                  80

Asp Ser Ala Asn Asn Val Val Tyr Lys Gln Tyr Glu Asp Met Val Val
                 85                  90                  95

Glu Ser Cys Gly
            100

<210> SEQ ID NO 24
<211> LENGTH: 102
<212> TYPE: PRT
<213> ORGANISM: Homo sapiens

<400> SEQUENCE: 24

Cys Ser Lys Lys Pro Leu His Val Asn Phe Lys Glu Leu Gly Trp Asp

```
1               5                   10                  15
Asp Trp Ile Ile Ala Pro Leu Glu Tyr Glu Ala Tyr His Cys Glu Gly
            20                  25                  30

Leu Cys Glu Phe Pro Leu Arg Ser His Leu Glu Pro Thr Asn His Ala
            35                  40                  45

Ile Ile Gln Thr Leu Met Asn Ser Met Asp Pro Gly Ser Thr Pro Pro
            50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
            85                  90                  95

Glu Ser Cys Gly Cys Arg
            100
```

```
<210> SEQ ID NO 25
<211> LENGTH: 102
<212> TYPE: PRT
<213> ORGANISM: Bos Taurus

<400> SEQUENCE: 25

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Phe His Cys Glu Gly
            20                  25                  30

Val Cys Asp Phe Pro Leu Arg Ser His Leu Glu Pro Thr Asn His Ala
            35                  40                  45

Ile Ile Gln Thr Leu Met Asn Ser Met Asp Pro Gly Ser Thr Pro Pro
            50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Asn Glu Tyr Glu Glu Met Val Val
            85                  90                  95

Glu Ser Cys Gly Cys Arg
            100
```

```
<210> SEQ ID NO 26
<211> LENGTH: 102
<212> TYPE: PRT
<213> ORGANISM: Mus musculus

<400> SEQUENCE: 26

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
            35                  40                  45

Val Ile Gln Thr Leu Met Asn Ser Met Asp Pro Glu Ser Thr Pro Pro
            50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
            85                  90                  95

Glu Ser Cys Gly Cys Arg
            100
```

<210> SEQ ID NO 27
<211> LENGTH: 102
<212> TYPE: PRT
<213> ORGANISM: Artificial Sequence
<220> FEATURE:
<223> OTHER INFORMATION: danio mutant

<400> SEQUENCE: 27

```
Cys Ser Lys Lys Pro Leu His Val Asn Phe Arg Glu Leu Gly Trp Asp
1               5                   10                  15

Asp Trp Val Ile Ala Pro Leu Asp Tyr Glu Ala Tyr His Cys Glu Gly
            20                  25                  30

Met Cys Asp Phe Pro Leu Arg Ser His Leu Glu Pro Thr Asn His Ala
        35                  40                  45

Ile Ile Gln Thr Leu Met Asn Ser Met Asn Pro Ser Asn Met Pro Pro
    50                  55                  60

Ser Cys Cys Val Pro Ser Lys Leu Ser Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100
```

<210> SEQ ID NO 28
<211> LENGTH: 102
<212> TYPE: PRT
<213> ORGANISM: Danio rerio

<400> SEQUENCE: 28

```
Cys Ser Lys Lys Ala Leu His Val Asn Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Asn Ser Thr Pro Pro
    50                  55                  60

Ser Cys Cys Val Pro Thr Lys Leu Ser Pro Ile Ser Ile Leu Tyr Ile
65                  70                  75                  80

Asp Ser Gly Asn Asn Val Val Tyr Lys Gln Tyr Glu Asp Met Val Val
                85                  90                  95

Glu Gln Cys Gly Cys Arg
            100
```

<210> SEQ ID NO 29
<211> LENGTH: 102
<212> TYPE: PRT
<213> ORGANISM: Xenopus laevis

<400> SEQUENCE: 29

```
Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala His His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asn Pro Gly Ser Thr Pro Pro
    50                  55                  60
```

```
Ser Cys Cys Val Pro Thr Lys Leu Thr Pro Ile Ser Ile Leu Tyr Ile
 65                  70                  75                  80

Asp Ala Gly Asn Asn Val Val Tyr Lys Gln Tyr Glu Asp Met Val Val
                 85                  90                  95

Glu Ser Cys Gly Cys Arg
            100
```

<210> SEQ ID NO 30
<211> LENGTH: 102
<212> TYPE: PRT
<213> ORGANISM: Homo sapiens

<400> SEQUENCE: 30

```
Cys Ser Arg Lys Pro Leu His Val Asp Phe Lys Glu Leu Gly Trp Asp
 1               5                  10                  15

Asp Trp Ile Ile Ala Pro Leu Asp Tyr Glu Ala Tyr His Cys Glu Gly
             20                  25                  30

Leu Cys Asp Phe Pro Leu Arg Ser His Leu Glu Pro Thr Asn His Ala
         35                  40                  45

Ile Ile Gln Thr Leu Leu Asn Ser Met Ala Pro Asp Ala Ala Pro Ala
     50                  55                  60

Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                 85                  90                  95

Glu Ala Cys Gly Cys Arg
            100
```

<210> SEQ ID NO 31
<211> LENGTH: 102
<212> TYPE: PRT
<213> ORGANISM: Cercopithecus aethiops

<400> SEQUENCE: 31

```
Cys Ser Arg Lys Pro Leu His Val Asp Phe Lys Glu Leu Gly Trp Asp
 1               5                  10                  15

Asp Trp Ile Ile Ala Pro Leu Asp Tyr Glu Ala Tyr His Cys Glu Gly
             20                  25                  30

Val Cys Asp Phe Pro Leu Arg Ser His Leu Glu Pro Thr Asn His Ala
         35                  40                  45

Ile Ile Gln Thr Leu Leu Asn Ser Met Ala Pro Asp Ala Ala Pro Ala
     50                  55                  60

Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                 85                  90                  95

Glu Ala Cys Gly Cys Arg
            100
```

<210> SEQ ID NO 32
<211> LENGTH: 102
<212> TYPE: PRT
<213> ORGANISM: Macaca fascicularis

<400> SEQUENCE: 32

```
Cys Ser Arg Lys Pro Leu His Val Asp Phe Lys Glu Leu Gly Trp Asp
 1               5                  10                  15

Asp Trp Ile Ile Ala Pro Leu Asp Tyr Glu Ala Tyr His Cys Glu Gly
```

```
                    20                  25                  30

Val Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 33
<211> LENGTH: 102
<212> TYPE: PRT
<213> ORGANISM: Mus musculus

<400> SEQUENCE: 33

Cys Ser Arg Lys Ser Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 34
<211> LENGTH: 102
<212> TYPE: PRT
<213> ORGANISM: Gallus gallus

<400> SEQUENCE: 34

Cys Ser Arg Lys Pro Leu His Val Asn Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
            35                  40                  45

Ile Ile Gln Thr Leu Met Asn Ser Met Asp Pro Glu Ser Thr Pro Pro
        50                  55                  60

Ser Cys Cys Val Pro Ser Lys Leu Ser Pro Ile Ser Ile Leu Tyr Ile
65                  70                  75                  80

Asp Ser Gly Asn Asn Val Val Tyr Lys Gln Tyr Glu Asp Met Val Val
                85                  90                  95

Glu Thr Cys Gly Cys Arg
            100

<210> SEQ ID NO 35
<211> LENGTH: 102
<212> TYPE: PRT
```

-continued

```
<213> ORGANISM: Danio rerio

<400> SEQUENCE: 35

Cys Ser Arg Lys Pro Leu His Val Asn Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
        35                  40                  45

Ile Ile Gln Thr Leu Met Asn Ser Met Asp Pro Glu Ser Thr Pro Pro
    50                  55                  60

Ser Cys Cys Val Pro Ser Lys Leu Ser Pro Ile Ser Ile Leu Tyr Ile
65                  70                  75                  80

Asp Ser Gly Asn Asn Val Val Tyr Lys Gln Tyr Glu Asp Met Val Val
                85                  90                  95

Glu Ser Cys Gly Cys Arg
                100
```

GROWTH FACTOR MUTANTS WITH IMPROVED BIOLOGICAL ACTIVITY

CROSS REFERENCE TO RELATED APPLICATION

This application is a 35 USC §371 National Phase Entry Application from PCT/EP2006/001966, filed Mar. 3, 2006, and designating the United States.

The invention relates to novel recombinant biosynthetic growth factor mutants which exhibit improved biological activity. Said improved protein activity is achieved by the substitution of specific amino acids of the original growth factor proteins which are naturally occurring of the transforming growth factor-beta superfamily of signalling molecules. The recombinant proteins provided herein are particularly suitable for regeneration, growth stimulation and differentiation of various cells, tissues and organs. The invention also relates to nucleic acid molecules coding for said recombinant protein mutants, expression vectors and host cells containing the nucleic acid molecules, antibodies directed against said protein mutants, pharmaceutical compositions and methods for producing the growth factor mutants.

The transforming growth factor-beta (TGF-beta) superfamily of proteins comprises more than 35 members including TGF-betas, bone morphogenetic proteins (BMPs), activins, inhibins and growth/differentiation factors (GDFs). TGF-beta superfamily proteins promote cell proliferation and differentiation as well as tissue formation and are relevant for a wide range of medical treatment methods and applications. These dimeric molecules act through specific receptor complexes that are composed of type I and type II serine/threonine receptor kinases. The receptor kinases subsequently activate Smad proteins, which then propagate the signals into the nucleus to regulate target gene expression. Smad independent signalling pathways are also initiated by these receptors and result in induction of the MAP Kinase pathway. Smads are a unique family of signal transduction molecules that can transmit signals directly from the cell surface receptors to the nucleus, where they regulate transcription by interacting with DNA binding partners as well as transcriptional coactivators and corepressors.

The members of this protein family are initially synthesized as large heterogeneous precursor proteins which subsequently undergo proteolytic cleavage at a cluster of basic residues approximately 110-140 amino acids from the C-terminus, thus releasing the C-terminal mature protein parts from the N-terminal prodomain. All mature polypeptides are structurally related and contain a conserved bioactive domain comprising six or seven canonical cysteine residues which are responsible for the characteristical three-dimensional "cysteine-knot" motif of these proteins.

The various superfamily members can be further classified into distinct subfamilies and -groups, based on the extent of the homology/identity of their cystine-knot motif. The overlapping families of bone morphogenetic proteins and growth/differentiation factors (GDFs) are known to play a diverse set of roles in the skeletal system and other tissues (see i.e. Ducy and Karsenty 2000, Kidney Int. 57, 2207-2214 for a review). Especially human GDF-5 (the protein is also known as MP52, CDMP-1 or sometimes as BMP-14), GDF-6 (CDMP-2, BMP13) and GDF-7 (CDMP-3, BMP-12) have been grouped together by several authors due to their comparable biological properties and the extraordinarily high degree of amino acid sequence identity (see i.e. Mikic 2004, Annals of Biomedical Engineering 32, 466-476; Wolfman et al. 1997, J. Clin. Invest. 100, 321-330).

Besides the prominent functions of the GDF-5/-6/-7 subgroup in the de novo formation of bone and cartilage (Cheng et al. 2003, J. Bone & Joint Surg. Am. 85-A, 1544-1552; Settle et al. 2003, Developm. Biol. 254, 116-130), it has repeatedly been demonstrated that the members of this subgroup are also important inducers and regulators of tendon and ligament (Wolfman et al. 1997, J. Clin. Invest. 100, 321-330), nerve tissues (Farkas et al. 1997, Neurosci Lett. 236, 120-122; Watakabe et al. 2001, J. Neurochem. 76, 1455-1464), periodontal ligament and teeth (Sena et al 2003, J. Dent. Res. 82, 166-171; Morotome et al. 1998, Biochem. Biophys. Res. Commun. 244, 85-90), and other tissues.

The gene and protein structures of various naturally occurring BMPs/GDFs including GDF-5, GDF-6 and GDF-7 have previously been elucidated. Several loss-of function mutants of GDF-5 could be identified which i.e. lead to shortening of fingers and toes (brachydactyly type C) and other skeletal abnormalities such as brachypodism in animals (Storm et al. 1994, Nature 368, 639-643) and acromesomelic displasias in man (Thomas et al. 1996, Nature Gen. 12, 315-317). Regarding these mutants it has been found that specific amino acid substitutions at positions 173, 204, 400, 438, 441 and 498 of human GDF-5 either reduce or completely abolish the protein function (Schwabe et al. 2004, Amer. J. Med Genet. 124A, 356-363). In contrast, only very few GDF-mutants with enhanced biological activity are known to date. A rare example is disclosed in WO01/11041 and relates to active monomeric GDF-5 which lacks the cysteine residue normally responsible for dimerization.

The search for the molecules responsible for bone-, cartilage-, and other tissue-inductive activity has led to the discovery of a set of molecules called growth/differentiation factors. Due to their unique tissue inductive activities these proteins have been successfully applied in therapeutic research and regenerative surgery in which they promote and assist the natural healing process of damaged tissues, either alone or in combination with specific carrier and/or matrix materials. Nevertheless there is a great need to develop improved and more efficient forms of these proteins for such purposes.

This object is solved according to the invention by providing novel recombinant proteins derived from GDF-5-related proteins which exhibit improved biological activity as described herein and in the attached claims.

Some frequently used terms herein are defined and exemplified as follows:

The term "cysteine-knot-domain" as used herein means the well known and conserved cysteine-rich amino acid region which is present in the mature parts of TGF-beta superfamily proteins such as human GDF-5 and which forms a three-dimensional protein structure known as cysteine-knot. In this domain, the respective location of the cysteine residues to each other is important and is only allowed to vary slightly in order not to lose the biological activity. Consensus sequences for cysteine-knot domains are known in the state of the art. According to the definition defined herein the cysteine-knot-domain of a protein starts with the first cysteine residue participating in the cysteine-knot of the respective protein and ends with the residue which follows the last cysteine participating in the cystine-knot of the respective protein. For example, the cystine-knot domain of the human GDF-5 precursor protein (SEQ ID NO 1) comprises the amino acids 400-501 (see also FIG. 1).

The term "GDF-5-related protein" as used herein means any naturally occurring or artificially created protein which comprises a cysteine-knot-domain with an amino acid identity of at least 70% to the 102 aa cysteine-knot domain of human GDF-5 (amino acids 400-501 of FIG. 1/SEQ ID NO 1) and which carries arginine, serine and asparagines residues at positions equivalent to residues arginine 438 (R438), serine 439 (S439) and asparagine 445 (N445) of human GDF-5. Included are proteins belonging to the group of GDF-5, GDF-6 and GDF-7 proteins from vertebrate or mammalian species as well as recombinant variants thereof as long as these proteins fulfil the above mentioned requirement.

Non-limiting examples of GDF-5 related proteins are human GDF-5 (disclosed as MP52 in WO95/04819 and in Hötten et al. 1994, Biochem. Biophys Res. Commun. 204, 646-652), recombinant human GDF-5/MP52 (WO96/33215), mouse GDF-5 (U.S. Pat. No. 5,801,014), CDMP-1 (WO96/14335), HMW human MP52s (WO97/04095), rabbit GDF-5 (Sanyal et al. 2000, Mol Biotechnol. 16, 203-210), human GDF-6/BMP-13 (U.S. Pat. No. 5,658,882), bovine GDF-6 (NCBI accession no P55106), mouse GDF-6 (NCBI accession no NP_038554), GDF-6/CDMP-2 (WO96/14335), human GDF-7/BMP-12 (U.S. Pat. No. 5,658,882), mouse GDF-7 (NCBI accession no MP97721), GDF-7/CDMP-3 (WO96/143335), chicken GDF-5 (NCBI accession no. NP_989669), *Xenopus laevis* GDF-5 (NCBI accession no. AAT99303), monomeric GDF-5, -6 and -7 (WO 01/11041 and WO99/61611), as shown in FIGS. 3 and 4.

The term "RSN-mutant" as used herein means a recombinant protein derived from a GDF-5-related protein in which, after alignment with human GDF-5 as described in this application, the amino acid equivalent to arginine 438 (R438) of human GDF-5 (SEQ ID NO 1) is not arginine (R) and/or in which the amino acid equivalent to serine 439 (S439) of human GDF-5 is not serine (S), and/or in which the amino acid equivalent to asparagine 445 (N445) is not asparagine (N).

The term "improved biological activity" as used herein relates to a biological activity of a RSN-mutant amounting at least 120% of the activity of the respective non-mutated protein.

The term "biological activity" denotes the biological activities of a GDF-5 related protein. For example, this activity can be measured by one or more of the following assays:
a) Osteogenic and chondrogenic activity can be measured by an in vitro alkaline phosphotase assay (ALP), e.g. as described in Takuwa et al. (1989), Am. J. Physiol. 257, E797-E803);
b) Neurotrophic activity can be determined by increased survival of dopaminergic neurons as described for example by Krieglstein et al. 1995 (J. Neuroscience Res. 42, 724-732) or Sullivan et al. 1997 (Neuroscience Letters 233, 73-76);
c) the outgrowth of nerve fibers can be measured from embryonic retina as described i.e. in WO97/03188;
d) the angiogenic potential of these proteins can be determined for example in an in vivo corneal micropocket model as described in Yamashita et al. 1997 (Exp. Cell Research 235, 218-226);
e) effects of GDF-5-related proteins on the terminal differentiation of myoblasts is described e.g. by Inada et al 1996 (Biochem Biophys Res Commun. 222, 317-322);
f) in vivo tests measuring the inductive potential of such proteins concerning tendon and ligament e.g. are disclosed in Wolfman et al. 1997, J. Clin. Invest. 100, 321-330);
g) measurement of the signal transduction cascade through the activation of Smads using a reportergene assay based on the Smad-binding-elements preceding the firefly luciferase gene e.g. are previously described in Nohe et al., 2002. J Biol Chem. 277, 5330-5338.

The term "variant" as used herein means any of the following polypeptides:
a) biologically active fragments of a protein
b) protein constructs which contain additional sequences in excess to the original sequence of the protein
c) any combination of a) and b)

The GDF-5/-6/-7 group of TGF-beta superfamily proteins, comprising GDF-5 as its best characterized member, is highly conserved among vertebrate/mammalian species (Ducy and Karsenty 2000, Kidney Int. 57, 2207-2214). Several residues in these proteins are present in all group members and are therefore commonly believed to be critical for the biological function of the protein, i.e. the 13 amino acids equivalent to aa 435-447 of human GDF-5 (see FIG. 2.). Previous studies confirmed a loss of the protein functionality if amino acids present in this region are replaced. For example, substitution of the arginine residue present at position 438 by cysteine (mutation R438C, Polinkovsky et al. 1997, Nat Genet. 17, 18-19) and substitution of leucine 441 by proline (Fayaz-UI Haque et al. 2002, Clin. Genet. 61, 454-458) abolishes the protein function.

It has now surprisingly been found by means of mutational studies and other experiments that amino acid residues which correspond to arginine 438 (R438), serine 439 (S439) and asparagine 445 (N445) of human GDF-5 can be substituted with some specified amino acids without negative effects on the protein function. Moreover, these substitutions even increase the biological activity of the proteins significantly.

This embodiment of the invention is further illustrated by the FIGS. 1, 2 and 3. FIG. 1 shows the human GDF-5 precursor protein (Hötten et al. 1994, Biochem. Biophys Res. Commun. 204, 646-652) which consists of a 381 aa prodomain (aa 1-381 including aa 1-27, bold letters) and a 120 aa mature part (aa 382-501). Only the mature part and especially the cysteine-knot-domain (aa 400-501, underlined) are important for the biological function of the protein. Residues R438, S439 and N445 (grey boxes) are located within this cysteine-knot domain. Corresponding arginine, serine and asparagine residues in the cysteine-knot-domains of other GDF-5-related proteins are shown in FIG. 2 and FIG. 3 (marked by arrows). Corresponding residues in proteins not shown in these figures can be easily determined by a sequence alignment with human GDF-5.

It has been found in GDF-5-related proteins that when the arginine residue at a position corresponding to arginine 438 (R438) of human wild-type GDF-5 (SEQ. ID NO 1) is replaced with an amino acid chosen from alanine, valine, leucine, isoleucine, glycine, methionine, asparagine, the resulting recombinant protein has increased biological activity.

In a preferred embodiment, the chosen amino acid is leucine for the position R438.

It has also been found that when the serine residue at positions corresponding to serine 439 (S439) of human wild-type GDF-5 (SEQ. ID NO 1) is replaced with an amino acid chosen from aspartic acid, glutamic acid, glycine, leucine or isoleucine, either independently, or in combination with a replacement of R438, the resulting recombinant protein has increased biological activity.

In a preferred embodiment, the chosen amino acid is aspartic acid for the position S439.

It has further been found that the asparagine residue at positions corresponding to asparagine 445 (N445) of human wild-type GDF-5 (SEQ. ID NO 1) is replaced with an amino acid chosen from serine and threonine, either independently or in combination with either or both replacements of R438 and S439, the resulting recombinant protein has increased biological activity.

In a preferred embodiment, the chosen amino acid is threonine for position N445.

These (arginine/serine/threonine) RSN-mutants of GDF-5-related proteins in which the R438 and/or S439 and/or N445 equivalents are substituted with the amino acids specified above exhibit a biological activity greatly outperforming the activity of the respective nonmutated proteins.

As an example, FIG. 5 shows the ability of hGDF-5 RSN-mutant R438L to induce alkaline phosphatase in vitro. The mutant protein exhibits a biological activity between 145.6% (at 75 nM) and 177.4% (at 35 nM) of the activity of wildtype protein (rh-GDF-5) in this assay (average of two experiments). The minimal activity measured for the mutant at a single protein concentration and in a single experiment was 120% of the activity of the wild type protein.

Thus, encompassed by the invention are RSN-mutants which exhibit an improved biological activity amounting to at least 120% of the activity of the respective non-mutated protein. Especially preferred are GDF-5-related RSN-mutants with improved biological activities of at least 130%, more preferably at least 135%, more preferably at least 140%, more preferably at least 150%, more preferably at least 160%, more preferably at least 170%, more preferably at least 180%, more preferably at least 200% of the biological activity of the respective non-mutated protein.

The biological activities of GDF-5-related proteins and RSN-mutants thereof i.e. in the field of induction of bone, cartilage and connective tissue such as i.e. periodontal ligament can be easily determined with the help of established test systems. Most useful and preferred is a common in vitro test known as alkaline phosphatase (ALP) assay (Takuwa et al. 1989, Am. J. Physiol. 257, E797-E803), which is demonstrated in example 2/FIG. 5. GDF-5-related proteins have been demonstrated to increase alkaline phosphatase activity i.e. in ROB-C26 osteoprogenitor cells (Yamaguchi et al. 1991, Calcif. Tissue Int. 49, 221-225) as described in WO95/04819, in embryonic ATDC5 cells (Riken Gene Bank, ROB 0565), in mouse stromal MCHT-1/26 cells, and in periodontal ligament (HPDL) cells as shown in Nakamura et al. 2003, J. Periodontal Res. 38, 597-605.

The GDF-5-related proteins as defined herein comprise a cysteine-knot-domain with an amino acid identity of at least 70%, preferably at least 75%, preferably at least 80%, more preferably at least 85%, more preferably at least 90%, more preferably at least 95%, to the 102 aa cysteine-knot domain of human GDF-5. This limiting value is well suitable to separate members of the GDF-5/-6/-7 group of proteins as well as variants thereof from further proteins such as other GDFs and BMPs. A comparison of the 102 aa cysteine-knot-domains of human GDF-5, human GDF-6 and human GDF-7 (FIG. 2) reveals the high grade of amino acid identity between these proteins. Human GDF-6 shares 87 (85%) and human GDF-7 83 (81%) identical residues with the cysteine-knot-domain of human GDF-5. The respective domains of GDF-5/-6/-7 molecules from other vertebrate and mammalian species which have been identified so far also show very high identity percentages of at least 75% (between 79% and 99%), when compared with human GDF-5 (FIG. 4). In contrast, GDFs and BMPs not belonging to the GDF-5/-6/-7 subgroup display much lower identity values below 60%.

The determination of corresponding amino acid positions in related amino acid sequences as well as the calculation of percentages of identity between can be performed with the help of well known alignment algorithms and optionally computer programs using these algorithms. The amino acid identities in this patent application have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in:

Thompson, J. D., Gibson, T. J., Plewniak, F., Jeanmougin, F. and Higgins, D. G. (1997)

ClustalX is a windows interface for the ClustalW multiple sequence alignment program and is i.e. available from various sources, i.e. by anonymous ftp from the University of Strasbourg, the European Molecular Biology Laboratory, the European Bioinformatics Institute or via download from the University of Strasbourg webpage. The ClustalW program and algorithm is also described in detail in:

Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research 22:4673-4680.

The RSN-mutants of GDF-5-related proteins according to the invention are generally applicable in every indication in which GDF-5-related proteins such as GDF-5, GDF-6 and GDF-7 are also useful. It has been demonstrated that GDF-5-related proteins are important inducers and regulators/differentiators of i.e. bone and cartilage (Cheng et al. 2003, J. Bone & Joint Surg. Am. 85-A, 1544-1552; Settle et al. 2003, Developm. Biol. 254, 116-130), connective tissue such as tendon and ligament (Wolfman et al. 1997, J. Clin. Invest. 100, 321-330), nerve tissue (Farkas et al. 1997, Neurosci Lett. 236, 120-122; Watakabe et al. 2001, J. Neurochem. 76, 1455-1464), stem cells (Shimaoka et al. 2003, J. Biomed. Materials Res. Part A 68A, 168-176; Bai et al. 2004, Biochem. Biophys. Res. Commun. 325, 453-460) and/periodontal ligament and teeth (Sena et al 2003, J. Dent. Res. 82, 166-171; Morotome et al. 1998, Biochem. Biophys. Res. Commun. 244, 85-90).

In a preferred embodiment, the RSN-mutant comprises a sequence which matches one of the following generic amino acid sequences a) $CX_1X_2KX_3LHVX_4FX_5X_6X_7GWDDWX_8IAPLX_9YEAX_{10}HCX_{11}GX_{12}CX_{13}FPX_{14}Z_1SHLEPTN\ HAX_{15}IQTLX_{16}NSMX_{17}PX_{18}X_{19}X_{20}PX_{21}X_{22}CCVPX_{23}X_{24}LX_{25}PISILX_{26}X_{27}DX_{28}X_{29}NNVVYX_{30}X_{31}Y\ EX_{32}MVVEX_{33}CGCR$ [SEQ ID NO: 3] or b) $CX_1X_2KX_3LHVX_4FX_5X_6X_7GWDDWX_8IAPLX_9YEAX_{10}HCX_{11}GX_{12}CX_{13}FPX_{14}RZ_2HLEPTN\ HAX_{15}IQTLX_{16}NSMX_{17}PX_{18}X_{19}X_{20}PX_{21}X_{22}CCVPX_{23}X_{24}LX_{25}PISILX_{26}X_{27}DX_{28}X_{29}NNVVYX_{30}X_{31}Y\ EX_{32}MVVEX_{33}CGCR$ [SEQ ID NO: 4] or c) $CX_1X_2KX_3LHVX_4FX_5X_6X_7GWDDWX_8IAPLX_9YEAX_{10}HCX_{11}GX_{12}CX_{13}FPX_{14}RSHLEPTZ_3\ HAX_{15}IQTLX_{16}NSMX_{17}PX_{18}X_{19}X_{20}PX_{21}X_{22}CCVPX_{23}X_{24}LX_{25}PISILX_{26}X_{27}DX_{28}X_{29}NNVVYX_{30}X_{31}Y\ EX_{32}MVVEX_{33}CGCR$ [SEQ ID NO: 5] or d) $CX_1X_2KX_3LHVX_4FX_5X_6X_7GWDDWX_8IAPLX_9YEAX_{10}HCX_{11}GX_{12}CX_{13}FPX_{14}Z_1Z_2HLEPTN\ HAX_{15}IQTLX_{16}NSMX_{17}PX_{18}X_{19}X_{20}PX_{21}X_{22}CCVPX_{23}X_{24}LX_{25}PISILX_{26}X_{27}DX_{28}X_{29}NNVVYX_{30}X_{31}YEX_{32}MVVEX_{33}CGCR$ [SEQ ID NO: 6] or e) $CX_1X_2KX_3LHVX_4FX_5X_6X_7GWDDWX_8IAPLX_9YEAX_{10}HCX_{11}GX_{12}CX_{13}FPX_{14}Z_1SHLEPTZ_3\ HAX_{15}IQTLX_{16}NSMX_{17}PX_{18}X_{19}X_{20}PX_{21}X_{22}CCVPX_{23}X_{24}LX_{25}PISILX_{26}X27DX28X29NNVVYX_{30}X_{31}YEX_{32}MVVEX_{33}CGCR$ [SEQ ID NO: 7] or f) $CX_1X_2KX_3LHVX_4FX_5X_6X_7GWDDWX_8IAPLX_9$
  $YEAX_{10}HCX_{11}GX_{12}CX_{13}FPX_{14}RZ_2HLEPTZ_3$
  $HAX_{15}IQTLX_{16}NSMX_{17}PX_{18}X_{19}X_{20}PX_{21}X_{22}CCVPX_{23}$
  $X_{24}LX_{25}PISILX_{26}X_{27}DX28X29NNVVYX_{30}X_{31}YEX_{32}$
  $MVVEX_{33}CGCR$ [SEQ ID NO: 8] or
g) $CX_1X_2KX_3LHVX_4FX_5X_6X_7GWDDWX_8IAPLX_9$
  $YEAX_{10}HCX_{11}GX_{12}CX_{13}FPX_{14}Z_1Z_2HLEPTZ_3HAX_{15}$
  $IQTLX_{16}NSMX_{17}PX_{18}X_{19}X_{20}PX_{21}X_{22}CCVPX_{23}X_{24}LX_{25}$
  $PISILX_{26}X27DX28X29NNVVYX_{30}X_{31}YEX_{32}MVVEX_{33}$
  $CGCR$ [SEQ ID NO: 9] or
and wherein
every X denotes any amino acid,
$Z_1$ denotes alanine (A), asparagine (N), glycine (G), isoleucine (I), leucine (L), methionine (M) or valine (V),
$Z_2$ denotes aspartic acid (D), glutamic acid (E), glycine (G), leucine (L) or isoleucine (I)
$Z_3$ denotes serine (S) or threonine (T)

| | |
|---|---|
| every X | denotes any amino acid, |
| $Z_1$ | denotes alanine (A), asparagine (N), glycine (G), isoleucine (I), leucine (L), methionine (M) or valine (V), |
| $Z_2$ | denotes aspartic acid (D), glutamic acid (E), glycine (G), leucine (L) or isoleucine (I) |
| $Z_3$ | denotes serine (S) or threonine (T) |

In a more preferred embodiment the RSN-mutant comprises a sequence which matches one of the above mention generic amino acid sequences and wherein

| | |
|---|---|
| $X_1$ | denotes asparagine (N) or serine (S) |
| $X_2$ | denotes arginine (R) or lysine (K) |
| $X_3$ | denotes alanine (A), glutamine (Q), proline (P) or serine (S) |
| $X_4$ | denotes asparagine (N) or aspartic acid (D) |
| $X_5$ | denotes arginine (R) or lysine (K) |
| $X_6$ | denotes aspartic acid (D) or glutamic acid (E) |
| $X_7$ | denotes leucine (L) or methionine (M) |
| $X_8$ | denotes isoleucine (I) or valine (V) |
| $X_9$ | denotes aspartic acid (D) or glutamic acid (E) |
| $X_{10}$ | denotes histidine (H), phenylalanine (F) or tyrosine (Y) |
| $X_{11}$ | denotes aspartic acid (D) or glutamic acid (E) |
| $X_{12}$ | denotes leucine (L), methionine (M) or valine (V) |
| $X_{13}$ | denotes aspartic acid (D) or glutamic acid (E) |
| $X_{14}$ | denotes isoleucine (I) or leucine (L) |
| $X_{15}$ | denotes isoleucine (I) or valine (V) |
| $X_{16}$ | denotes leucine (L) or methionine (M) |
| $X_{17}$ | denotes alanine (A), asparagine (N) or aspartic acid (D) |
| $X_{18}$ | denotes arginine (R), asparagine (N), aspartic acid (D), glutamic acid (E), glycine (G) or serine (S) |
| $X_{19}$ | denotes alanine (A), asparagine (N), serine (S) or threonine (T) |
| $X_{20}$ | denotes alanine (A), methionine (M) or threonine (T) |
| $X_{21}$ | denotes alanine (A) or proline (P) |
| $X_{22}$ | denotes serine (S) or threonine (T) |
| $X_{23}$ | denotes alanine (A), serine (S) or threonine (T) |
| $X_{24}$ | denotes arginine (R) or lysine (K) |
| $X_{25}$ | denotes serine (S) or threonine (T) |
| $X_{26}$ | denotes phenylalanine (F) or tyrosine (Y) |
| $X_{27}$ | denotes isoleucine (I) or threonine (T) |
| $X_{28}$ | denotes alanine (A) or serine (S) |
| $X_{29}$ | denotes alanine (A) or glyine (G) |
| $X_{30}$ | denotes asparagine (N) or lysine (K) |
| $X_{31}$ | denotes glutamic acid (E) or glutamine (Q) |
| $X_{32}$ | denotes aspartic acid (D) or glutamic acid (E), |
| $X_{33}$ | denotes alanine (A), glutamine (Q), serine (S) or threonine (T) |
| $Z_1$ | denotes alanine (A), asparagine (N), glycine (G), isoleucine (I), leucine (L), methionine (M) or valine (V) |
| $Z_2$ | denotes denotes aspartic acid (D), glutamic acid (E), glycine (G), leucine (L) or isoleucine (I) |
| $Z_3$ | denotes serine (S) or threonine (T) |

These generic sequences have been compiled from a comparison of the cysteine-knot domains of vertebrate GDF-5, GDF-6 and GDF-7 sequences according to FIG. 3. Positions which are not identical in all aligned proteins are denoted with an X in the generic sequences. Positions which are mutated according to the present invention are denoted with a Z.

In another preferred embodiment, the RSN-mutant protein according to the invention is an RSN-mutant of a vertebrate or recombinant GDF-5 protein or a variant thereof. Most preferred are RSN-mutants of a mammalian GDF-5 protein or variants thereof. Examples for vertebrate and mammalian GDF-5 proteins are: human GDF-5 (disclosed as MP52 in WO95/04819 and as human GDF-5 in Hötten et al. 1994, Biochem. Biophys Res. Commun. 204, 646-652), recombinant human GDF-5/MP52 (WO96/33215), recombinant monomeric GDF-5 (WO 01/11041 and WO99/61611), HMW human MP52s (WO97/04095), CDMP-1 (WO96/14335), mouse (*Mus musculus*) GDF-5 (U.S. Pat. No. 5,801,014), rabbit (*Oryctolagus cuniculus*) GDF-5 (Sanyal et al. 2000, Mol Biotechnol. 16, 203-210), chicken (*Gallus gallus*) GDF-5 (NCBI accession no. NP_989669), african clawed frog (*Xenopus laevis*) GDF-5 (NCBI accession no. AAT99303).

Enclosed in these embodiments are also RSN-mutants of allelic versions of the aforementioned genes/proteins as well as RSN-mutants of the vertebrate, mammalian and recombinant proteins or variants thereof having additional mutations such as substitutions, additions and deletions, as long as these additional mutations have no essential effect on protein activity.

In general, the RSN-mutant of the vertebrate or mammalian or recombinant GDF-5 protein or variant thereof is expected to show all already described activities of GDF-5 and can be applied wherever the above mentioned recombinant and wild-type GDF-5 forms are been successfully used. For example, GDF-5 is considered to be a very effective promoter of bone and cartilage formation as well as connective tissue formation (see for example WO 95/04819, Hötten et al. 1996, Growth Factors 13, 65-74; Storm et al. 1994, Nature 368, 639-643; Chang et al. 1994, J. Biol. Chem. 269, 28227-28234) and formation of connective tissue attachment (EP 0 831 884. In this context, GDF-5 is useful for applications concerning the joints between skeletal elements (see for example Storm & Kingsley 1996, Development 122, 3969-3979). One example for connective tissue is tendon and ligament (Wolfman et al. 1997, J. Clin. Invest. 100, 321-330; Aspenberg & Forslund 1999, Acta Orthop Scand 70, 51-54; WO 95/16035). The protein is helpful for meniscus and spinal/intervertebral disk repair (Walsh et al. 2004, Spine 29, 156-63) and spinal fusion applications (Spiro et al. 2000, Biochem Soc Trans. 28, 362-368). GDF-5 can be beneficially applied in tooth (dental and periodontal) applications (see for example WO 95/04819; WO 93/16099; Morotome et al. 1998, Biochem Biophys Res Comm 244, 85-90) such as the regeneration of dentin or periodontal ligament.

GDF-5 is also useful in wound repair of any kind. It is also beneficial for promoting tissue growth in the neuronal system and survival of e.g. dopaminergic neurons. In this context, GDF-5 can be used for treating neurodegenerative disorders like e.g. Parkinson's disease and possibly also Alzheimer's disease or Huntington chorea tissues (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). GDF-5 allows to maintain nervous function or to retain nervous function in already damaged tissues. GDF-5 is therefore considered to be a generally applicable neurotrophic factor.

It is also useful for diseases of the eye, in particular retina, cornea and optic nerve (see for example WO 97/03188; You et al. (1999), Invest Opthalmol Vis Sci 40, 296-311), for hair growth and the treatment and diagnosis of skin related disorders (WO 02/076494; Battaglia et al. 2002, Trans. Orthop. Res. Soc. 27, 584), and for induction of angiogenesis (Yamashita et al. 1997, Exp. Cell Res. 235, 218-26).

On the one hand, there is the prevention or therapy of diseases associated with bone and/or cartilage damage or affecting bone and/or cartilage disease, or generally situations, in which cartilage and/or bone formation is desirable or for spinal fusion, and on the other hand, there is prevention or therapy of damaged or diseased tissue associated with connective tissue including tendon and/or ligament, periodontal or dental tissue including dental implants, neural tissue including CNS tissue and neuropathological situations, tissue of the sensory system, liver, pancreas, cardiac, blood vessel, renal, uterine and thyroid tissue, skin, mucous membranes, endothelium, epithelium, for promotion or induction of nerve growth, tissue regeneration, angiogenesis, wound healing including ulcers, burns, injuries or skin grafts, induction of proliferation of progenitor cells or bone marrow cells, for maintenance of a state of proliferation or differentiation for treatment or preservation of tissue or cells for organ or tissue transplantation, for integrity of gastrointestinal lining, for treatment of disturbances in fertility, contraception or pregnancy.

Diseases concerning sensory organs like the eye are also to be included in the preferred indication of the pharmaceutical composition according to the invention. As neuronal diseases again Parkinson's and Alzheimer's diseases can be mentioned as examples.

Example 3 and FIG. 6 describe the results of an alkaline phosphatase assay with recombinant human GDF-5 (WO96/33215) and the RSN-mutant R438L (arginine substituted by leucine) of recombinant human GDF-5 (rhGDF-5). Recombinant human GDF-5 was used as a standard/control with 100% biological activity. The mutant protein exhibits a biological activity between 145.6% (at 75 nM) and 177.4% (at 35 nM) of the activity of wildtype protein (rh-GDF-5) in this assay (average of two experiments). The minimal activity measured for the mutant at a single protein concentration and in a single experiment was 120% of the activity of the wild type protein. Thus, in a preferred embodiment, RNS-mutants with improved biological activity which are encompassed by the invention have biological activities of at least 120% of the activity of human GDF-5 or recombinant human GDF-5 (WO96/33215) if determined in vitro via ALP assay. Especially preferred are GDF-5-related RSN-mutants with improved biological activities of at least 130%, more preferably at least 135%, more preferably at least 140%, more preferably at least 150%, more preferably at least 160%, more preferably at least 170%, more preferably at least 180%, more preferably at least 200% of the biological activity of the respective non-mutated protein.

The RSN-mutants according to the invention can be easily produced in various prokaryotic and eukaryotic expression systems, in particular by expression in prokaryotes and subsequent renaturation/refolding according to known methods (see i.e. WO96/33215).

A further subject matter of the present invention is a nucleic acid encoding an RSN-mutant according to the invention. The nucleic acid has a sequence such that a substitution of one or both residues equivalent to R438 and S439 of human GDF-5 with one of the amino acids specified in this application is achieved. The base triplets coding for these amino acids and the degeneracy of the genetic code are generally known. The nucleic acid can be a DNA sequence and/or a RNA sequence, as long as the protein according to the invention can be obtained from this nucleic acid upon expression in a suitable system.

Expression vectors are a further subject matter of the present invention, wherein the nucleic acid is inserted in a suitable vector system, the vector system being selected according to the desired expression of the protein. The vector system can be a eukaryotic vector system, but preferred is a prokaryotic vector system, with which the proteins can be produced in a particularly easy and pure manner. A suitable expression vector is i.e. shown in WO96/33215. The expression vector can also be a viral vector which can be used i.e. in gene therapy approaches.

Host cells are also a subject matter of the present invention. The host cells are characterized in that they contain a nucleic acid or an expression vector according to the invention and that they are able to use the information present in the nucleic acids and in the expression vector, respectively, for the expression of RSN-mutants according to the invention. Suitable host cells are preferably prokaryotic cells, in particular E. coli strains. Particularly useful host strains are descendents of E. coli W3110 as shown e.g. in WO96/33215. In a preferred embodiment, host cells, preferably of human origin, may also be useful for transplantation to patients in need thereof.

Another subject matter of the present invention are antibodies against RSN-mutants. These antibodies according to the present invention are specific for the claimed recombinant RSN-mutants. Preferably, they are specific for the cysteine knot regions of GDF-5 related proteins containing one or more of the amino acid replacements described herein. Preferably, the antibodies are specific for a region of a recombinant protein derived from a GDF-related protein according to the invention spanning amino acid 400-495, preferably 420-450, more preferably 425-440, more preferably amino acids 438-445. These antibodies according to the present invention can be generated by using those fragments of the protein of the invention as described above as immunogens to generate antibodies by known methods. The antibodies can be monoclonal or polyclonal and they can be of any isotype. Also comprised are antibody fragments such as Fab-fragments or $Fab_2$-fragments. The antibodies can also be humanized antibodies or chimeric antibodies etc.

Further subject matters of the present application are pharmaceutical and/or diagnostic compositions comprising at least one RSN-mutant of a GDF-5-related protein or a nucleic acid or a vector or host cell according to the invention. Suitable are generally all pharmaceutical composition which have already been published in context with GDF-5-related proteins. An expression vector or a host cell can be considered to be advantageous as active substances in a pharmaceutical and/or diagnostic composition. Also combinations of a protein according to the invention with other proteins can be used in preferred pharmaceutical compositions. Especially preferred for neuronal applications are combinations with other TGF-beta superfamily proteins such as i.e. GDNF (see WO 97/03188). For applications concerning cartilage and/or bone the combination with BMPs in general or with a cartilage maintenance-inducing protein such as BMP-9 (see e.g. WO 96/39170) is useful. Combinations with other proteins such as i.e. NGF, BDNF, EGF, PDGF, NT-3, -4, -5, chordin and/or hedgehog proteins are also possible (see i.e. WO97/03188). Of course this invention also comprises pharmaceutical compositions containing further substances like e.g. pharmacologically acceptable auxiliary and carrier substances. The formulation may include antioxidants, preservatives, colouring, flavouring and emulsifying agents, suspending agents, solvents, fillers, bulking agents, buffers, delivery vehicles, excipients and/or pharmaceutical adjuvants. For example, a suitable carrier or vehicle may be water for injection, physiological saline solution, or a saline solution mixed with a suitable carrier protein such as serum albumin. A preferred antioxidant for the preparation of the composition of the present invention is ascorbic acid.

Cosmetic compositions known in the art, preferably hypoallergic and pH controlled are especially preferred, and include toilet waters, packs, lotions, skin milks or milky lotions. Said preparations contain, besides the active compound, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

The solvent or diluent of the pharmaceutical composition may be either aqueous or non-aqueous and may contain other pharmaceutically acceptable excipients which are capable of modifying and/or maintaining a pH, osmolarity, viscosity, clarity, scale, sterility, stability, rate of dissolution or odour of the formulation. Similarily other components may be included in the pharmaceutical composition according to the present invention in order to modify and/or maintain the rate of release of the pharmaceutically effective substance. Such modifying components are substances usually employed in the art in order to formulate dosages for parenteral administration in either unit or multi-dose form. The finally formulated pharmaceutical and/or diagnostic composition prepared according to the present invention may be stored in sterile vials in form of a solution, suspension, gel, emulsion, solid or dehydrated or lyophilized powder. These formulations may be stored either in a ready-to-use form or in a form, e.g. in case of a lyophilized powder, which requires reconstitution prior to administration. The above and further suitable pharmaceutical formulations are known in the art and are described in, for example, Gus Remington's Pharmaceutical Sciences (18th Ed., Mack Publishing Co., Eastern, Pa., 1990, 1435-1712). Such formulations may influence the physical state, stability, rate of in vivo release and rate of in vivo clearance of the pharmaceutically effective component. Other effective administration forms comprise parenteral slow-release, i.e. retarded, formulations, inhalent mists, or orally active formulations. For example, a slow-release formulation may comprise proteins bound to or incorporated into particulate preparations of polymeric compounds (such as polylactic acid, polyglycolic acid, etc.) or liposomes. The pharmaceutical composition according to the present invention may also be formulated for parenteral administration, e.g., by infusion or injection, and may also include slow-release or sustained circulation formulations. Such parenterally administered therapeutic compositions are typically in the form of pyrogen-free, parenterally acceptable aqueous solutions comprising the pharmaceutically effective component(s) in a pharmaceutically acceptable carrier and/or diluent.

The pharmaceutical composition may comprise a matrix material, i.e. in cases where regeneration of bone or cartilage is intended. It is advantageous to the protein, the nucleic acid, the expression vector or the host cell when they are applied in and/or on a biocompatible matrix material. Matrix material as used herein means a carrier or matrix acting as a scaffold for cell recruitment, attachment, proliferation and differentiation and/or as a potential delivery and storage device for RSN-mutants. In contrast to the solid matrices, carriers consist of amorphous materials having no defined surfaces and lacking a specific shape, i.e. alkylcelluloses, pluronics, gelatins, polyethylene glycols, dextrins, vegetable oils, sugars and other liquid and viscous substances.

Uses of GDF-5-related proteins or similar morphogens such as as BMPs in combination with matrix materials are extensively published and described, such as for example in WO98/21972. These matrix materials are equally suitable for RSN-mutants according to the present invention. The matrix material can be transplanted into the patient, e.g. surgically, wherein the protein or the DNA encoding the protein can be slowly released from the matrix material and then be effective over a long period of time. All types of matrix materials are useful in accordance with the present invention, as long as they are biocompatible and selected for the intended area or indication of use. The matrix material can be a natural material, a modified natural material as well as a synthetic material. All already known matrices for morphogenetic proteins are encompassed. Examples of natural materials are e.g. autologous, heterologous or xenologous bone materials, collagen, e.g. collagen type I and III, or metals like titanium. Also other components of the extracellular matrix can be used. The extracellular matrix comprises for example the various collagens, as for example types I, II, V, IX, X, XI and XIII, further proteoglycanes and glycosaminoglycanes, as for example chondroitinsulfate, biglycane, decorine and/or hyaluronic acid, or noncollagenous proteins as for example osteopontin, laminin, fibronectin, vitronectin, thrombospondin, cartilage matrix protein and dentin phosphoprotein. All mentioned natural materials may also be used in artificially modified forms. Examples of modified natural materials are demineralized bone, thermoashed bone mineral, sintered bone or chemically crosslinked hyaluronic acid (hydrogel), or metal alloys. Examples of synthetic materials are polymers like polyglycolic acid, polylactide and polylactide derivatives such as e.g. polylactic acid, poly(lactide-co-glycolide), polylactid acid-polyethylene glycol or glycolide L-lactide copolymers, further polyphosphates, polyethylene glycol, polyoxyethylene polyoxypropylene copolymers or materials containing calcium phosphates such as beta-tricalcium phosphate ($Ca_3(PO_4)_2$), alpha-tricalcium phosphate and hydroxyl apatite. Further examples of other useful matrix materials belonging to one of the above mentioned groups are $Ca(OH)_2$, coral, natural bone mineral, chitin, non-demineralized bone particles, ceramic bone particles, ceramic dentin, irradiated cancellous bone chips, plaster of Paris, bioactive glass, apatite-wollastonite-containing glass ceramic. Also a combination of the above mentioned carriers and/or matrices can form the matrix material as for example the combination of hydroxy apatite and collagen (e.g. Healos, previously available from Orquest, Inc., CA, USA, [now DePuy Acromed, Mass., USA]), a combination of polyglycolic acid and polylactic acid or polylactid derivatives, or coral-collagen composites. For a non limiting list of useful carriers and matrices see further i.e. Kirker-Head 2000, Advanced Drug Delivery 43, 65-92.

The following non-limiting examples together with the figures and sequence protocols are intended to further illustrate the invention.

SEQ ID NOS 1 and 2 shows the protein and DNA sequences, respectively, of the human GDF-5 precursor. In the preferred human GDF-5 protein mutants with improved biological activity, the arginine residue at pos 438 and/or the serine residue at pos 439 and/or the asparagine residue at pos 445 are substituted with other amino acids.

FIG. 1 shows additional features of the human GDF-5 precursor protein according to SEQ ID NO: 1:

| | |
|---|---|
| aa 001-381 | pre-prodomain (bold letters) |
| aa 382-501 | mature protein part |
| aa 400-501 | cysteine-knot-domain (underlined) |
| aa 438-439 | residues arginine 438 and serine 439 (grey box) |
| aa 445 | residue asparagine 445 (grey box) |

FIG. 2 shows a comparison of the 102 aa cystine-knot-domains of human GDF-5 (SEQ ID NO 1; the 400-501 amino acid fragment), human GDF-6 (sequence 2 from U.S. Pat. No. 5,658,882; SEQ ID NO: 17) and human GDF-7 (sequence 26 from U.S. Pat. No. 5,658,882; SEQ ID NO: 18). Amino acid residues which are identical in all three molecules are highlighted in black. Residues R438, S439 of human GDF-5 and equivalent residues of human GDF-6 and GDF-7 are boxed and marked by arrows.

FIG. 3 shows a comparison of the 102 aa cystine-knot-domains of vertebrate GDF-5, -6 and -7 sequences from the genus *Homo*, further *Cercopithecus, Macaca, Bos, Mus, Gallus Danio* and *Xenopus*, which are available in the "Entrez" NCBI protein database (www.ncbi.nlm.nih.gov/Entrcz/ available at the National Library of Medicine, National Institutes of Health website) under the accession numbers shown in the figure. Residues R438 and S439 of human GDF-5 and equivalent residues of the other proteins are marked by arrows.

| Sequence Name | SEQ ID NO: |
|---|---|
| GDF-5 *Homo* P43026 | 19 |
| GDF-5 *Mus* NP 032135 | 20 |
| GDF-5 *Gallus* NP 989669 | 21 |
| GDF-5 *Danio* Y12005 | 22 |
| GDF-5 *Xenopus* AAT99303 | 23 |
| GDF-6 *Homo* P43028 | 24 |
| GDF-6 *Bos* P55106 | 25 |
| GDF-6 *Mus* NP 032135 | 26 |
| GDF-6 *Danio* NM 130987 | 27 |
| GDF-6 *Danio* AAB34226 | 28 |
| GDF-6 *Xenopus* AAD38402 | 29 |
| GDF-7 *Homo* P43029 | 30 |
| GDF-7 *Cercopithecus* Q9BDW8 | 31 |
| GDF-7 *Macaca* AAK27794 | 32 |
| GDF-7 *Mus* P43029 | 33 |
| GDF-7 *Gallus* AAC97113 | 34 |
| GDF-7 *Danio* AAD20829 | 35 |

FIG. 4 shows a table with the sequence identities of cysteine-knot-domains of known BMPs and GDFs to the cysteine-knot-domain of human GDF-5.

Figure 9:
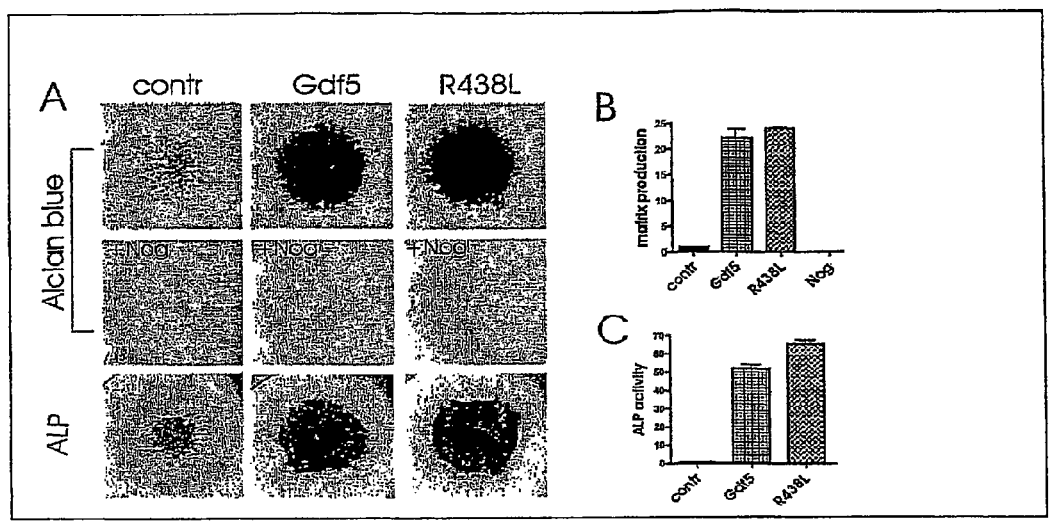

FIG. 9 shows the induction of cartilage production after infection of micromass cells with wildtype and mutant GDF5-expressing viruses (see example 4). Cartilage production is indicated by the increase in Alcian blue and ALP staining. (A) Chicken micromass cultures assayed after 4 days for extracellular matrix production and analysed after 7 days for ALP activity. Cells were infected with virus containing wildtype or mutant sequences and coinfection or not with BMP antagonist Noggin. Coinfection with Noggin (Nog) completely represses chondrogenesis irrespective of the Gdf5 variant expressed. (B) Alcian blue incorporation into the extracellular matrix of micromass cultures reflecting the production of proteoglycan-rich cartilaginous matrix measured at day 4. (C) ALP activity of micromass cultures at day 7.

Figure 10:
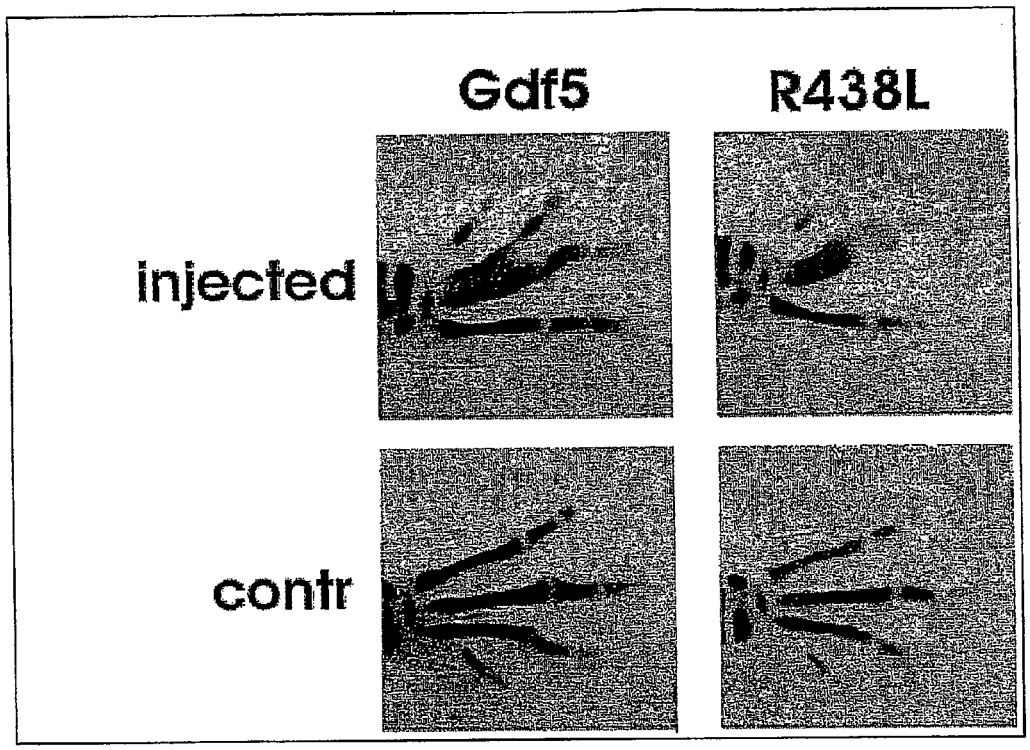

FIG. 10 shows overexpression of wildtype GDF-5 as well as GDF-5 mutant R438L in chick embryos according to example 5. Alcian blue staining was used to visualize cartilage. Uninfected limb is shown for comparison.

EXAMPLE 1

Creation, Expression and Purification of RSN-Mutants

DNAs coding for the mature parts of human GDF-5, human GDF-6 and human GDF-7 proteins have been isolated from human ROB-C26 osteoprogenitor cells (Yamaguchi et al. 1991, Calcif. Tissue Int. 49, 221-225) via RT-PCR technique and subsequently ligated into prokaryotic plasmid vectors. In order to identify functionally important amino acid residues in the mature parts of GDF-5, -6 and -7, various single mutations have been introduced into these sequences via site directed mutagenesis. All individual mutations were created by using the QuickChange™ site-directed mutagenesis kit with the PfuTurbo™ DNA polymerase and the DPN I endonuclease from Stratagene according to the instruction manual of the manufacturer.

Using the bacterial strain W3110BP transformed with the plasmids and induced with IPTG, the proteins were expressed in inclusion bodies. These inclusion bodies were isolated using a homogenization buffer (25 mM Tris HCl pH 7.3, 10 mM EDTA NaOH pH 8, 8 M Urea) and wash buffer (1 M Urea, 20 mM Tris HCl, pH 8.3, 10 mM EDTA NaOH pH 8.0) according to standard procedures. Further purification was carried out on a reversed phase column Aquapore Octyl (Applied Biosys, (CV=7.8 ml) 100×10, 20µ, No 186470) with a gradient from 100% of Eluent A (0.1% TFA, HPLC H2O) to 100% Eluent B (0.1% TFA, 90% CH3N, HPLC H2O) in 104 minutes (flow rate: 3 ml/min). After a western blot control, the fractions containing the mutant protein were pooled and lyophilized.

The mutant proteins were dissolved in dissolving buffer (6 M Guanidin HCl, 50 mM Tris, 150 mM NaCl, 3 mM DTT, pH=8.0), the protein concentration was exactly adjusted to 2.6 mg/ml and the pH was adjusted between 8 and 9. After 2 h incubation at room temperature, refolding buffer (1 M NaCl, 50 mM Tris, 5 mM EDTA, 1 mM GSSG, 2 mM GSH, 33 mM Chaps, pH=9.5) was added under gentle agitation to reach a final concentration of 0.16 mg/ml.

The solution was then incubated for 48 h at 22° C. and the refolding was stopped by changing the pH to 3-4 by adding 18% HCl. After centrifugation, the non-refolded monomer was separated from the dimer form by carrying out a second RP-HPLC under the same conditions. The fractions containing the dimerized protein were pooled, lyophilized and stored at −70° C.

EXAMPLE 2

Measurement of the Biological Activity of RSN-mutants in vitro by ALP Assay $1 \times 10^4$ cells of ATDC-5 cells were incubated overnight in 96-well plates in cell culture medium (alpha-MEM, Penicilline/Streptomycine, 2 mM L-glutamine, 10% FCS) at 37° C., 5% CO2, H2O-saturated. The next day, cells were stimulated with the GDF-5 related proteins and mutants thereof for 72 hrs with indicated ligand concentrations. The cells were subsequently washed with PBS (phosphate buffered saline). Cell lysis was performed in 100 ul alkaline lysis buffer 1 (0.1M glycine, pH 9.6, 1% NP-40, 1 mM MgCl2, 1 mM ZnCl2) for 1 h at room temperature. Then 100 ul alkaline lysis buffer 2 was added (0.1M glycine, pH 9.6, 1 mM MgCl2, 1 mM ZnCl2+2 mg/ml PNPP). The plates were incubated at 37° C., 5% $CO_2$, $H_2O$-saturated. The ALP-reaction was stopped afterwards with 100 µl of 30 g/l NaOH and finally the optical density was measured with an automatic microplate reader at 405 nm under consideration of blank value subtraction.

Figure 3:
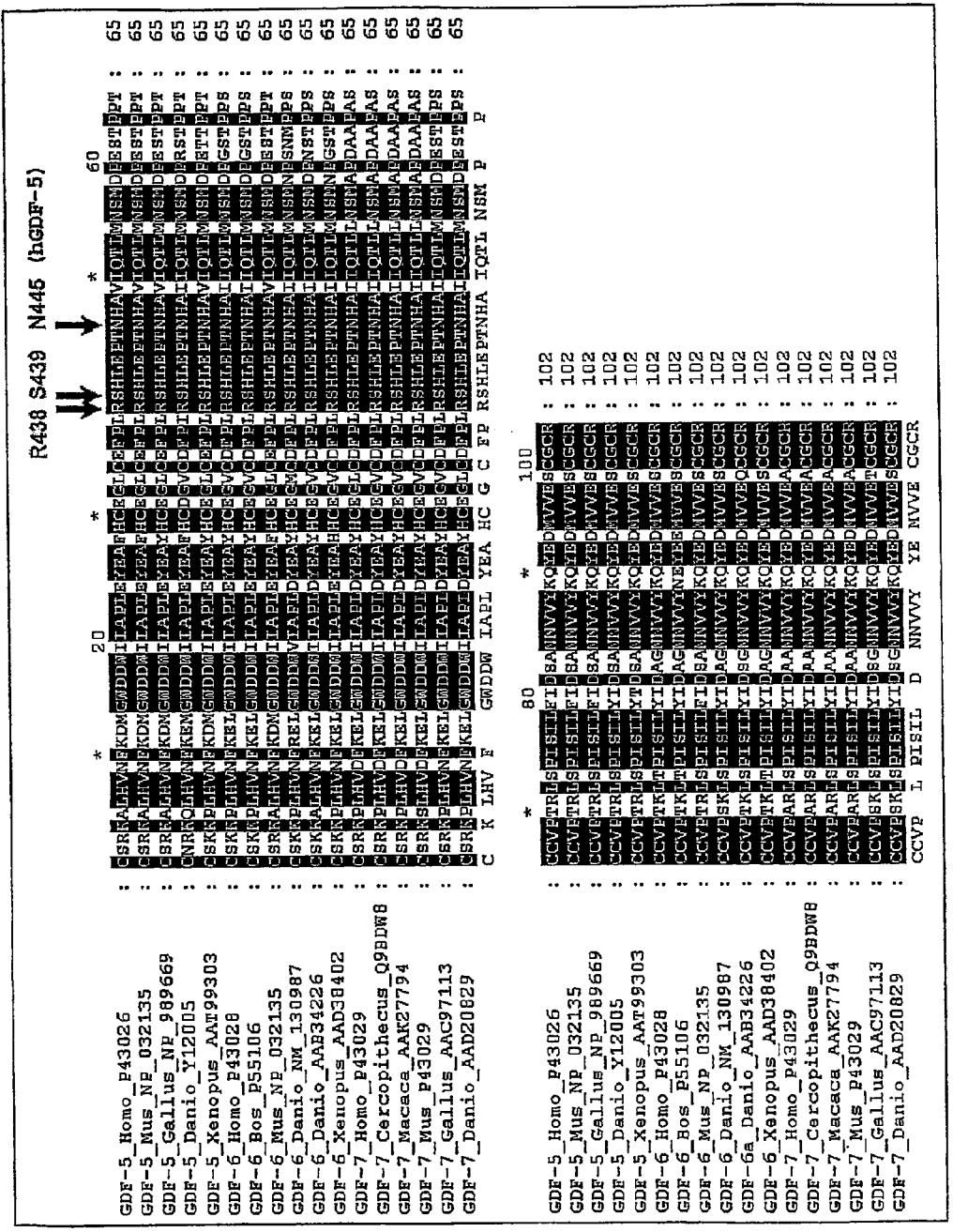
Figure 5:
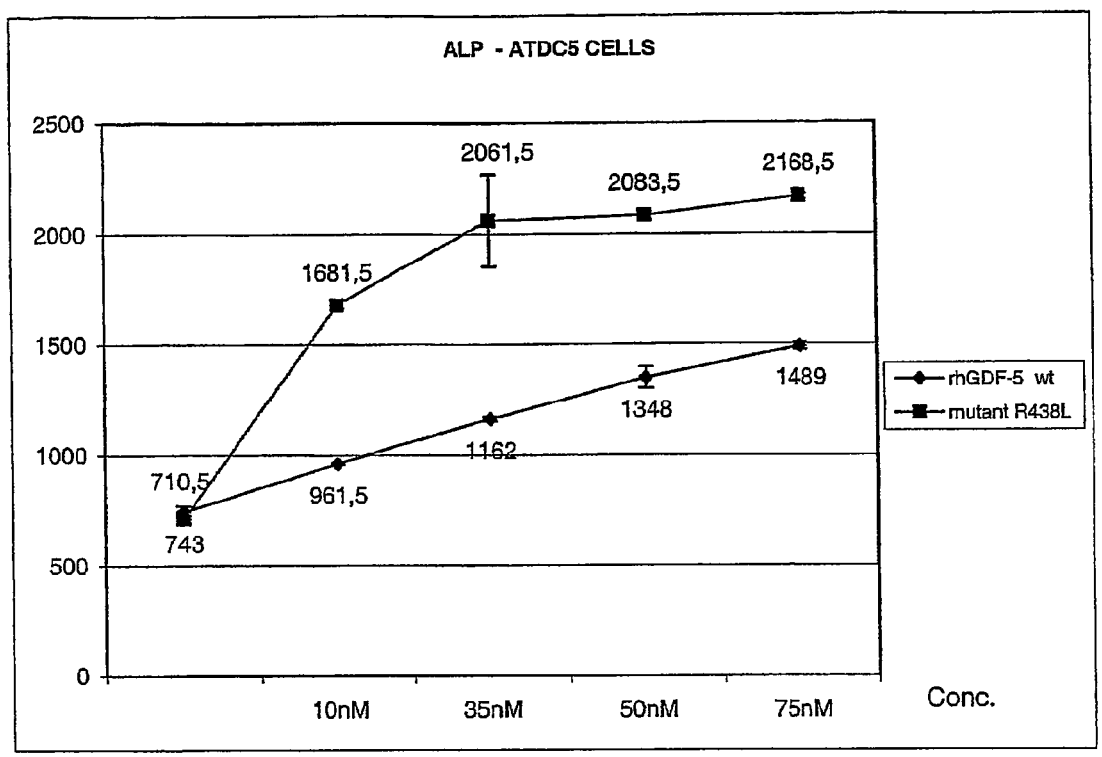
FIG. 5 shows the results of an alkaline phosphatase assay (ALP) with recombinant human GDF-5 (rh-GDF-5) and hGDF-5 RSN-mutant R438L (as described in example 2).

As an example, results (average values of 2 independent experiments) regarding hGDF-5 mutant R438L are shown in FIG. 5. Four different protein concentrations (10 nM, 35 nM, 50 nM, 75 nM) have been used in this assay. The mutant protein exhibits a averaged biological activity between 145.6% (2168.5/1489 at 75 nM) and 177.4% (2061.5/1162 at 35 nM) of the activity of wildtype protein (rh-GDF-5) in this assay system.

EXAMPLE 3

Ectopic Bone Formation in a Subcutaneous Rat Model

In this study, the GDF-5 mutant R438L was compared to wt GDF-5 and to BMP-2 in a rat subcutaneous implant model for ectopic bone forming potential. Fifty-four 4-5 week old outbred male Sprague Dawley rats were randomized into 9 groups (n=6 per group). Each animal was implanted with one test material and a contralateral control. Graft materials were prepared in advance of surgery as following: rhBMP-2 (R&D Systems), rhGDF-5 (Biopharm GmbH, Heidelberg, Germany) or rhGDF-5 R438L (Biopharm GmbH, Heidelberg, Germany) were lyophilized onto 5×5×5 mm Collagen Type I sponges (Helistat, Integra LifeSciences Corp). Helistat alone was used as contralateral controls in each animal. Implants were thawed prior to implantation.

The following test materials and morphogen amounts were evaluated:

| Test Material | Dose, µg/implant (µg/cc) | | |
| --- | --- | --- | --- |
| rhBMP-2 | 1 (7) | 2 (13) | 7.5 (50) |
| Wt rhGDF-5 | 7.5 (50) | 15 (100) | 75 (500) |
| rhGDF-5 R438L | 7.5 (50) | 15 (100) | 75 (500) |

Two subcutaneous pockets were created in the ventral thoracic region of each rat. One pocket was filled with one of the nine treatment groups, while the other was filled with Helistat alone. At 21 days post-surgery, all rats were euthanized and plain radiographs of the thoracic area were taken. The explants were removed and given a rating (0: very soft to 3: hard) based on gross observation, and cut in half. One half of each explant was placed in a tube and frozen at −80° C. for alkaline phosphatase analysis, while the other half was fixed in 10% neutral buffered formalin for histological analysis. Histomorphometric analyses was performed on all samples. Briefly, bone quantity, fibrosis and inflammation were rated from 0 to 4, based on percent tissue present (0:0%; 1: up to 25%; 2: between 25% and 50%; 3: between 50% and 75% and 4: between 75% and 100%).

Figure 6:
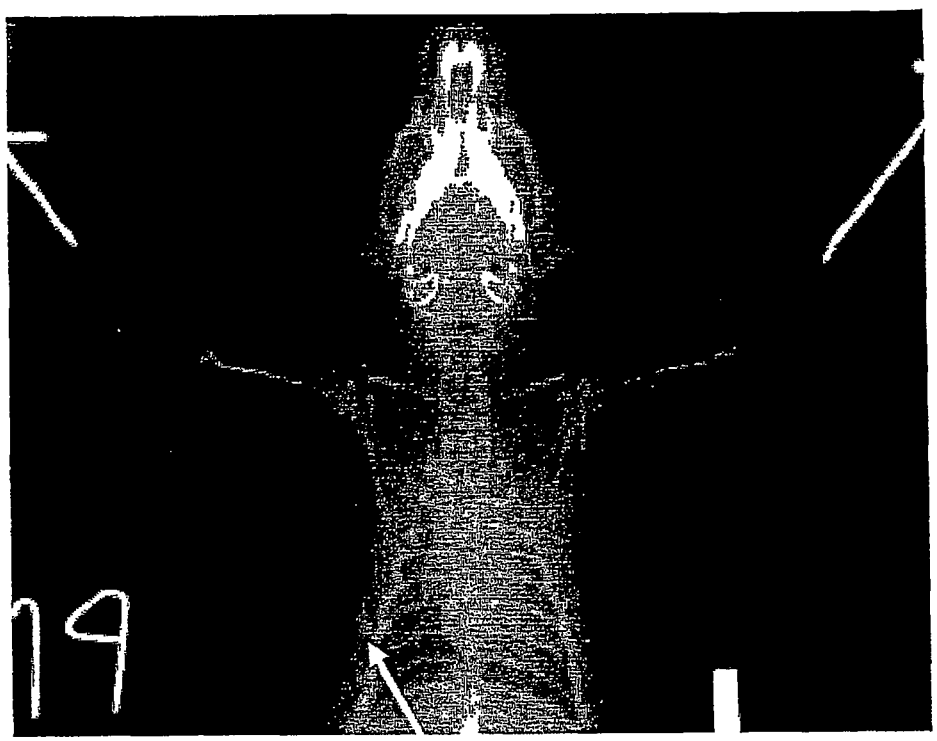
FIG. 6 shows ectopic bone formation in a subcutaneous rat model as described in example 3. Visible calcification (arrow) was detected only in the subcutaneous pocket filled with rhGDF-5 mutant R438L at 75 µg/implant.
Figure 7:
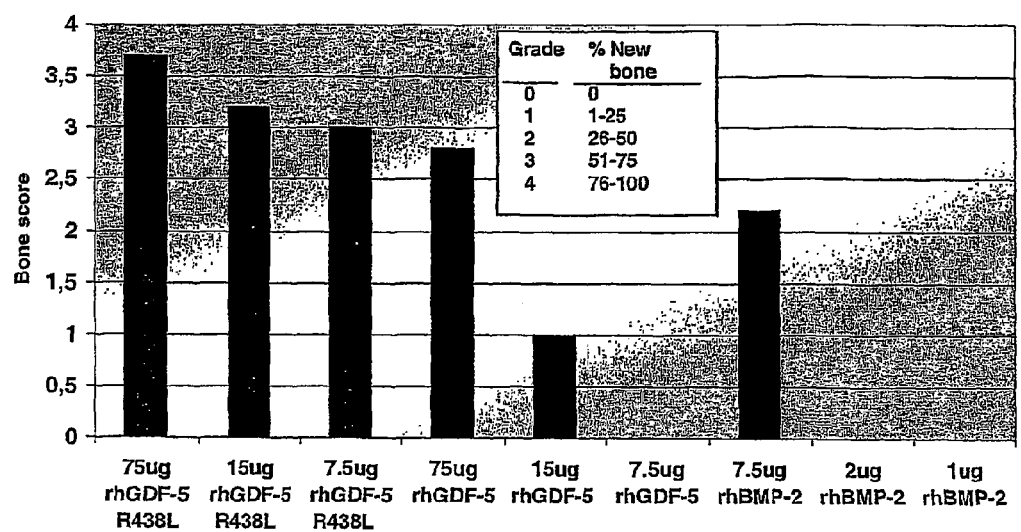
FIG. 7 shows bone quantity scores as described in example 3.
Figure 8:
FIG. 8 shows a histological example of new bone formation as induced with 75 µg/per implant rhGDF-5 mutant R438L according to example 3.

Results: All animals survived the procedures well and completed the 21-day postoperative period. By gross observation, none of the implants containing either 1 µg or 2 µg rhBMP-2 were rated firm. However, 5 out of 6 implants containing 7.5 µg rhBMP-2 were firm. In the wt rhGDF-5 group, only 1 sample per group in the 7.5 µg and the 15 µg group were firm. However, all 6 samples in the 7.5 µg group were firm. In the rhGDF-5 R438L group, 5 out of 6 samples in the 7.5 µg group was rated firm. All 6 samples in the 15 µg and all 6 samples in the 75 µg groups were rated firm. Radiographic assessments showed visible calcification only in animals implanted with rhGDF-5 R438L at 75 µg/implant (FIG. 6). Histomorphometric analyses demonstrated highest bone scores for rhGDF-5 R438L, as well as 75 µg dose implants of wt rhGDF-5 and 7.5 µg rhBMP-2 (see FIG. 7 and FIG. 8). In addition, in vivo alkaline phosphatase activity was mostly observed in 5 groups: in implants containing rhGDF-5 R438L (at all evaluated doses), 75 µg rhGDF-5, and 7.5 µg rhBMP-2.

EXAMPLE 4

Functional Analysis of GDF-5 Mutant Proteins in Micromass Culture

To analyze the functional consequences of the GDF5 mutations chicken micromass cultures were infected with the RCAS viruses expressing WT and mutated Gdf5. Cell differentiation and cartilaginous matrix production were determined by measurement of alkaline phosphatase (ALP) and Alcian blue. Alcian blue incorporation into the extracellular matrix of micromass cultures reflects the production of proteoglycan-rich cartilaginous matrix. Briefly, the coding sequence of chicken Gdf5 was cloned into pSLAX-13 and used as a template for generating the mutations R438L and L441P corresponding to the human mutations. In vitro mutagenesis was done using the Quickchange Kit (Stratagene) with according to the manufacturer's recommendations. Cloning into the RCAS-Vector was performed as described previously (Hughes, S. H., Greenhouse, J. J., Petropoulos, C. J., and Sutrave, P. 1987. Adaptor plasmids simplify the insertion of foreign DNA into helper-independent retroviral vectors. J Virol 61:3004-3012). RCAS-Nog was a kind gift from A. Vortkamp. Micromass cultures were performed as described previously (Lehmann, K., Seemann, P., Stricker, S., Sammar, M., Meyer, B., Suring, K., Majewski, F., Tinschert, S., Grzeschik, K. H., Muller, D., et al. 2003. Mutations in bone morphogenetic protein receptor 1B cause brachydactyly type A2. Proc Natl Acad Sci USA 100:12277-12282.) with minor modifications. Briefly, fertilized chicken eggs were obtained from Tierzucht Lohmann (Cuxhaven, Germany) and incubated at 37.5° C. in a humidified egg incubator for about 4.5 days. Ectoderm was removed and cells were isolated from the limb buds at stage HH23/24 by digestion with 0.1% collagenase type la and 0.1% trypsine. Micromass cultures were plated at a density of 2×105 cells per 10 µl drop. Infection was performed with 1 µl of the concentrated viral supernatants, RCASBP-A containing the cDNA encoding WT-chGdf5, R438L-chGdf5 and RCASBP-B containing the cDNA encoding WT chNog. Culture medium (DMEM-F12, 2% chicken serum, 4 mM L-glutamine, penicillin (1000 U/ml) and streptomycin (100 µg/ml)) was replaced every 2 days.

As expected, infection of micromass cells with WT GDF5 expressing virus results in a induction of cartilage production as indicated by the increase in Alcian blue and ALP staining (FIG. 9). Infection with the GDF mutants such as rhGDF R438L results in strong induction of Alcian blue and ALP.

Treatment of the infected cultures with bone morphogenetic protein antagonist noggin completely inhibits cartilage formation in the WT, as well as in the mutant constructs.

EXAMPLE 5

Expression Analysis During Joint Development and Overexpression of GDF5 in vivo

Overexpression of wildtype GDF-5, as well as the GDF-5 mutants was done in chick embryos using RCAS retroviral system. Production of concentrated viral supernatant and injection into the limb field of HH10 chicken embryos was performed as described previously (Stricker, S., Fundele, R., Vortkamp, A., and Mundlos, S. 2002. Role of Runx genes in chondrocyte differentiation. Dev Biol 245:95-108.) The same virus preparations were used as for the micromass cultures. Embryos were harvested between stages HH32-35 and stained with Alcian blue to visualize cartilage. In situ hybridization was performed on 7 μm sections of paraffin embedded mouse limbs, stage E13.5 and E14.5, by using digoxygenin labeled riboprobes as described (Stricker, S., Fundele, R., Vortkamp, A., and Mundlos, S. 2002. Role of Runx genes in chondrocyte differentiation. Dev Biol 245:95-108). Enlargement of skeletal elements and joint fusions in infected limbs at stage HH32 could be demonstrated in limbs infected with wildtype GDF5 and especially with GDF-5 mutants (see for example GDF-5 R438L in FIG. 10). Uninfected limb is shown for comparison.

The invention claimed is:

1. A recombinant protein comprising a cysteine-knot-domain with an amino acid according to the 102 aa cysteine-knot domain of human GDF-5 (amino acids 400-501 of FIG. 1/SEQ ID NO 1), wherein
   a) the amino acid at the position corresponding to arginine 438 (R438) of human wild-type GDF-5 (SEQ ID NO 1) is substituted with an amino acid selected from the group consisting of glycine, alanine, valine, leucine, isoleucine, methionine and asparagine, or
   b) the amino acid at the position corresponding to serine 439 (S439) of human wild-type GDF-5 (SEQ ID NO 1) is substituted with an amino acid selected from the group consisting of aspartic acid, glutamic acid, glycine, leucine and isoleucine, or
   c) the amino acid at the position corresponding to asparagine 445 (N445) of human wild-type GDF-5 (SEQ ID NO 1) is substituted with an amino acid selected from the group consisting of serine and threonine, or any combination thereof.

2. The recombinant protein according to claim 1, where the amino acid at the position corresponding to arginine 438 (R438) of human wild-type GDF-5 (SEQ ID NO: 1) is leucine.

3. The recombinant protein according to claim 1 which is a GDF-5-related protein.

4. The recombinant protein according to claim 3, wherein the GDF-5-related protein is a vertebrate GDF-5 protein or a variant or an allelic version thereof.

5. The recombinant protein according to claim 4, wherein the GDF-5-related protein is human GDF-5 (SEQ ID NO 1) or a variant thereof.

6. A pharmaceutical composition comprising a protein according to claim 1.

7. A pharmaceutical composition according to claim 6, wherein the protein is contained in or on a biocompatible matrix material.

8. Pharmaceutical composition according to claim 6, additionally comprising pharmacologically acceptable auxiliary or carrier substances, or a combination thereof.

9. A pharmaceutical composition according to claim 6, in a form suitable for the therapy of injuries or the therapy of diseases in connection with damaged bone or cartilage.

10. A method for the production of a recombinant protein according to claim 1 comprising recombinantly preparing a protein derived from a GDF-5-related protein by
   a) replacing the amino acid at the position corresponding to arginine 438 (R438) of human wild-type GDF-5 (SEQ ID NO 1) with glycine, alanine, valine, leucine, isoleucine, methionine or asparagine, or
   b) replacing the amino acid at the position corresponding to serine 439 (S439) of human wild-type GDF-5 (SEQ ID NO 1) with aspartic acid, glutamic acid, glycine, leucine or isoleucine or
   c) replacing the amino acid at the position corresponding to asparagine 445 (N445) of human wild-type GDF-5 (SEQ ID NO 1) with serine or threonine, or any combination thereof.

11. A method for the therapy of a disease associated with bone or cartilage damage or a disease effecting bone or cartilage, or any combination of said diseases, in a patient in need of such therapy, or a combination thereof, said method comprising administering to said patient an effective amount of a protein according to claim 1.

12. A method of promoting cartilage and/or bone formation and/or spinal fusion in a patient in need thereof, said method comprising administering to said patient an effective amount of a protein according to claim 1.

13. A method for the therapy of damaged or diseased tissue associated with connective tissue including tendon and/or ligament, and periodontal or dental tissue including dental implants, in a patient in need thereof, said method comprising administering to said patient an effective amount of a protein according to claim 1.

14. A method for improving the joints of skeletal elements and/or for meniscus and/or spinal/intervertebral disk repair in a patient in need thereof, said method comprising administering to said patient an effective amount of a protein according to claim 1.

* * * * *